US005607676A

United States Patent [19]
Gevas et al.

[11] Patent Number: 5,607,676
[45] Date of Patent: *Mar. 4, 1997

[54] IMMUNOGENIC COMPOSITIONS AGAINST GASTRIN PEPTIDES

[75] Inventors: Philip C. Gevas, Honolulu, Hi.; Stephen L. Karr; Stephen Grimes, both of Davis, Calif.; Richard L. Littenberg, Kai Lua, Hi.

[73] Assignee: Aphton Corporation, Woodland, Calif.

[*] Notice: The portion of the term of this patent subsequent to Jun. 11, 2008, has been disclaimed.

[21] Appl. No.: 721,638

[22] PCT Filed: Jan. 23, 1990

[86] PCT No.: PCT/US90/00520

§ 371 Date: Jul. 22, 1991

§ 102(e) Date: Jul. 22, 1991

[87] PCT Pub. No.: WO90/08774

PCT Pub. Date: Aug. 9, 1990

Related U.S. Application Data

[63] Continuation-in-part of Ser. No. 351,193, May 12, 1989, abandoned, which is a continuation-in-part of Ser. No. 301,353, Jan. 24, 1989, Pat. No. 5,023,077.

[51] Int. Cl.$^6$ .................. C07K 5/00; A61K 39/00; A61K 39/385; A61K 38/00
[52] U.S. Cl. .................. 424/197.11; 424/184.1; 530/324; 530/325; 530/326; 530/327; 530/328; 530/329; 530/330; 530/309; 514/12; 514/13; 514/14; 514/15; 514/16; 514/17; 514/18
[58] Field of Search .................. 424/88, 197.11, 424/184.1; 530/326, 327, 328, 329, 330, 309; 514/13, 14, 15, 16, 17, 18, 12

[56] References Cited

U.S. PATENT DOCUMENTS

| | | | |
|---|---|---|---|
| 3,931,141 | 1/1976 | Wissman et al. | 530/329 |
| 4,384,995 | 5/1983 | Stevens | 260/112.5 |
| 4,526,716 | 7/1985 | Stevens | 260/112.5 |
| 4,565,805 | 1/1986 | Smirnov et al. | 514/17 |
| 4,687,759 | 8/1987 | Martinez et al. | 514/18 |
| 4,691,006 | 9/1987 | Stevens | 530/324 |
| 5,023,077 | 6/1991 | Bevas et al. | 424/88 |

OTHER PUBLICATIONS

Kothary et al.; Identification of Progastria–17, *Biochem. Biophys Res Comm* 146 (2): 884–888; 1987.
Larsson et al; Characterization of Antial Gasterin Cells with Region–Specific Antisera; *J Histochem & Cytochem*, 25: 1317–1321 (1977).
Nemeth, Developm of a RIA by using N–term 1–13 antibody, *Chem Abst* 98: 51653W, p. 495 (1982).
Dockray, Immunochem Studies on Big Gastrin Using NH–Term Specific Antiserum *Chem Abst* 94; 119200 W, p. 506 (1980).
Azuma et al. 1986. Immunocytochemical evidence for differential distribution . . . Gastroenterologia japonica 21(4): 319–24.
Kothany et al. 1987 NH$_2$–Terminal of Gastrin–17 Induodenal Ulcer Disease . . . BBRC 146(2): 884–88.
Dockray et al 1975. Amino Terminal Gastrin Fragment in Serum . . . Gastroenterology 68: 222–230.
Nemeth et al. 1982. Development of a Sequence–Specific . . . Chem. Abstracts 1983 98: 51653W p. 495.
Iwanaga et al. 1980. Immunocytochemical Localization of the Different . . . Biomedical Res. 1: 316–320.
Dockray 1980. Immunochemical Studies on Big Gastrin . . . Chemical Abstracts (1981) 94: 119200W p. 506.
Larsson et al. 1977. Characterization of Antral Gastrin Cells with Region–Specific Antisera J. Histochem. & Cytochem. 25(12):1317–21.
Iwanaga et al; Immunocytochemical Localization of the Different Gastrin Forms in the Pyloric Antrum; *Biomed Res* 1: 316–320 (1980).
Nemeth, et al., Izotoptechnika 25: 288–294, 1982.
Rae–Venter et al., Gastroenterology 80: 1256, 1986.
Sugano et al., The Journal of Biological Chemistry, vol. 260, No. 21, Sep. 25, 1985, pp. 11724–11729.
Jaffe et al., Gastroenterology, vol. 58, No. 2, Feb. 1970, pp. 151–156.
Jaffe et al., Surgery, vol. 69, No. 2, Feb. 1971, pp. 232–237.
Jaffe et al., Surgery, vol. 65, No. 4, Apr. 1969, pp. 633–639.
Hughes et al., Digestive Diseases, vol. 21, No. 3, Mar. 1976, pp. 201–204.
Larsson, Neuohistochemoistry: Modern Methods and Applications, 1986, pp. 527–567.
Moroder et al., Gastrin and Cholecystokinin, Chemistry, Physiology and Pharmacology, 1987, pp. 21–32.
Dockray et al., Gastroenterology, vol. 68, No. 2, Feb. 1975, pp. 222–230.
Choudhury et al., Z. Physiol. Chem., Nov. 1980, pp. 1719–1733.
Azuma et al. Gastroenteologia Japonica, vol. 21, No. 4, Aug. 1986, pp. 319–324.
Varndell et al., Experientia, 39, 1983, pp. 713–717.
Rehfeld et al. Scand. J. Clin. Lab. Invest., 30, 1972, pp. 221–232.
De Magistris et al., Analytical Biochemistry, 102, 1980, pp. 126–133.
Rehfeld et al., Regulatory Peptides, 2, 1981, pp. 333–342.
Yamaguchi, K., et al., Chem. Abs., 100: 154661m, pp. 373, (1983).
Dockray, "Regulatory Peptides", 1, 169–186 (1980).

(List continued on next page.)

*Primary Examiner*—James C. Housel
*Assistant Examiner*—N. M. Minnifield
*Attorney, Agent, or Firm*—White & Case

[57] ABSTRACT

Immunogenic compositions useful for the treatment of ulcers or tumors whose growth is dependent on or stimulated by gastrin hormones are disclosed. The immunogenic compositions induce antibodies in a subject which selectively neutralize the specific hormones. Pharmaceutical compositions comprising effective amounts of the immunogenic compositions and methods of treatment using the compositions are disclosed. A method of reversing the inventive treatments by neutralizing the antibodies induced in vivo is also disclosed.

13 Claims, 11 Drawing Sheets

OTHER PUBLICATIONS

Yanaihara et al., "Biomedical Research", 1, 242–247.
Yanaihara et al., "Gut Peptides", 26–33 (1979).
Beauchamp et al., Ann. Surg., 202, Sep. 1985, pp. 303–309.
Lamote et al., Regulatory Peptides, 20, 1988, pp. 1–9.
Lamers et al., Eur. J. Cancer Clin. Oncol., vol. 24., No. 2, 1988, pp. 267–273.
Watson et al., in vitro, Br. J. Surg., vol. 75, Apr. 1988, pp. 342–345.
Kusyk et al., Am. J. Physiol., 251, 1986, pp. G597–G601.
Weinstock et al., Cancer Research, 48, Feb. 15, 1988, pp. 932–937.
Upp et al., Cancer Research, 49, Jan. 15, 1989, p. 488.
Smith et al., Digestive Diseases and Science, vol. 34, No. 2, Feb. 1989, pp. 171–174.
Smith et al., Gastroenterology, 95 1988, pp. 1541–1548.
Upp et al. Ann. Surg. vol. 207, No. 6, Jun. 1988 pp. 662–669.
Upp et al., Ann. Surg. vol. 207, No. 6, Jun. 1988 pp. 662–669.

IMMUNOGENIC COMPOSITIONS AGAINST GASTRIN PEPTIDES

This application is a continuation-in-part of application Ser. No. 07/351,193, filed May 12, 1989, now abandoned, which is a continuation-in-part of application Ser. No. 07/301,353, filed Jan. 24, 1989 and issued Jun. 11, 1991 as U.S. Pat. No. 5,023,077.

BACKGROUND OF THE INVENTION

Peptic ulcer disease exists in two forms, duodenal ulcers and gastric ulcers. Central to the cause of duodenal ulcers, is the production of excess stomach acid and pepsin and a rapid gastric emptying time. This results in an increase in duodenal exposure to secreted acid and enzymes, and in mucosal damage.

The second form of the disorder, gastric ulcer disease, may be caused by increased stomach acid and a breakdown of the complex stomach defenses that normally protect the gastric mucosa from acid damage. Although the two conditions have different etiologies, both benefit from a reduction in gastric acid secretion.

Because excess stomach acid is a central cause of ulcers, antacid preparations are commonly used as one method of treatment. This method merely neutralizes stomach acid after it is produced. Consequently, large quantities of antacids must be consumed on an ongoing basis to neutralize acid which is continually produced in the stomach. Antacids do not cure the disease because they do not affect the source of acid production.

Gastric acid is produced in a specialized stomach cell, the parietal cell. Parietal cells can be stimulated to secrete acid by acetylcholine, histamine and gastrin, upon the binding of each of these compounds with specific receptors on the surface of the cell. Of these the most potent stimulator of acid secretion is the peptide hormone gastrin.

Current approaches to the control and cure of peptic ulcers center upon devising drugs that inhibit the ability of one or more of these compounds to stimulate acid production or secretion. The most effective group of drugs approved for sale are the H2 antagonists (e.g. Tagamet® and Zantac®) which block the histamine H2 receptors on gastric parietal cells and inhibit acid secretion. These drugs, however, require relatively large doses on a daily basis and may induce several undesirable side effects. In cases where H2 antagonists have cured ulcers, relapses occur in almost 100% of cured individuals within a year of discontinuation of treatment. Other drugs have also exhibited problems, including low efficacy and unacceptable levels of toxicity. In the case the peptide hormone gastrin, no successful chemical antagonists have been identified.

Gastrin has several important functions in the gastrointestinal tract, the two most important being stimulation of acid secretion and stimulation of the growth of cells in the gastrointestinal tract. The hormone exists in at least two molecular forms, heptadecagastrin ("$G_{17}$") and tetrateseracontagastrin ("$G_{34}$") named according to the number of amino acid ("AA") residues in each molecule. $G_{34}$ and $G_{17}$ are identical in structure at the carboxy terminus, which is the binding site of the hormones with receptors. $G_{17}$ constitutes the 17 carboxy terminal ("C-terminal") end residues of $G_{34}$. $G_{34}$ consists of the 17 C-Terminal end residues which comprise $G_{17}$ and an additional different amino acid sequence of 17 amino terminal ("N-terminal") residues. When $G_{34}$ is split by trypsin a $G_{17}$ subunit and a non-hormonal 17 amino acid subunit results. Though $G_{17}$ is usually obtained by trypsin cleavage of $G_{34}$, each form may also be generated separately from its own prohormone.

Although $G_{17}$ and $G_{34}$ are thought to be equipotent on a molar basis as stimulator of acid release, $G_{34}$ is most probably responsible for the stimulation of growth of the gastrointestinal mucosa and the maintenance of the basal acidity of the stomach. $G_{34}$ is the principal form present during interdigestive periods. $G_{34}$ has a serum half life approximately six times as long as $G_{17}$ (40 minutes versus 6 minutes) and is produced in both the stomach and the duodenum. Alternatively, $G_{17}$ is the primary stimulator of meal-induced gastric acid secretion. $G_{17}$ is 1500 times more potent than histamine and makes up 90% of the antral (stomach) gastrin. $G_{17}$ accounts for roughly 60%–70% of the gastrin-mediated acid release.

The prior art in the area of gastrin immunology mainly concerns the induction of antibodies useful for identifying anatomic sites containing or producing gastrin $G_{17}$ or $G_{34}$ in laboratory animals; see Sugano, K., et al., 1985, "Identification and characterization of glycine-extended post translational processing intermediates of progastrin in porcine stomach", *J. of Biological Chemistry* 250: 11724–11729; Vaillant, C., et al., 1979, "Cellular origins of different forms of gastrin: The specific immunocytochemical localization of related peptides. *J. Histochem Cytochem* 27:932–935; Larsson, L. I. et al., 1977, "Characterization of antral gastrin cells with region-specific antisera". *J. Histochem. Cytochem* 25: 1317–1321. The antisera reported in these publications contained antibodies of numerous specificities, for a variety of antigenic epitopes on gastrin molecules.

Attempts to control gastrin levels by anti-gastrin antibodies induced by active immunization or passive administration of preformed antibodies such as those reported in Jaffe, B. M., et al., 1971, "Gastrin resistance following immunizations to the C-terminal tetrapeptide amide of gastrin, *Surgery* 69: 232–238; Jaffe, B. M., et al., 1970, "Inhibition of endogenous gastrin activity by antibodies to the carboxyl terminal tetrapeptide amide of gastrin", *Gastroenterology* 58: 151–156; Jaffe et al., 1969, "Inhibition of endogenous gastrin activity by incubation with antibodies to the C-terminal tetrapeptide of gastrin. *Surgery* 65: 5633–639 are different from the present invention in that the immunogen used was derived from the carboxyl terminal tetra-peptide amino acid sequence common to $G_{17}$, $G_{34}$, and to another important hormone, cholecystokinin ("CCK"). The immunogen of Jaffe et al. is thus of no practical value as an anti-gastrin vaccine component; on the contrary, it would produce a deleterious state in which all gastrin activity and other hormone function of $G_{17}$, $G_{34}$, together with CCK, would be blocked and eliminated by immunization.

This invention provides a novel immunological approach to the control and regulation of gastrin induced disorders such as peptic ulcers. According to the invention, antibodies are induced in the patient by active immunization with immunogens that selectively target specific forms of gastrin. Alternatively, the patient can be passively immunized with anti-gastrin antibodies specific for certain forms of gastrin.

In addition to peptic ulcers, other diseases appear to be related to the hormonal and stimulatory effects of gastrin. These diseases may also be treated by the selective anti-gastrin treatment of the invention.

An area of major medical importance for which the neutralization of gastrin hormonal activity has great therapeutic potential concerns the control of tumors and pathological conditions that are stimulated by gastrointestinal hormones. Several cancers of the gastrointestinal tract and associated tissues are stimulated to grow by the trophic action of gastrin. See Lamers, C.S.H.S., and Jansen, J.B.M.S., 1988, "Role of Gastrin and Cholecystokinin in Tumours of the Gastrointestinal Tract", *Eur. J. Cancer Clin. Oncol.* 22: 267–273. Gastrin promotes the growth of colon carcinoma, gastric carcinoma and gastric carcinoids. Gastrin antagonists may inhibit the growth of human colon cancer and enhance host survival as has been shown in mice; see, Beauchamp, R. O., et. al. 1985, "Proglumide, A Gastrin Receptor Antagonists, Inhibits Growth Of Colon Cancer And Enhances Survival In Mice." *Ann. Surg.* 202: 303–309. The neutralization of gastrin tumor promoting activity may provide an important therapy for these diseases.

A second important application of gastrin neutralization therapy concerns conditions in which the hormone is overproduced. Certain cancers of the gastrointestinal tract, apudomas, produce extremely large quantities of gastrin. In either case, the excess hormone produced by the apudoma or pituitary tumor will have adverse physiologic effects on organs or tissues containing receptors for the hormone. Excess gastrin production by apudomas stimulates hypertrophy of the acid secreting epithelium of the stomach, leading to excess stomach acid secretion, peptic ulcer, and neoplastic changes in the epithelium.

Available treatment for tumors stimulated by gastrin and for tumors that produce gastrin consists primarily of surgical resection of the cancerous tissue. This approach is frequently unsuccessful; in many instances the tumors cannot be located or are present in anatomic sites that are inoperable. In most instances these tumors do not respond well to radiation or chemotherapy regimens. New treatments are needed to supplement present procedures.

A therapeutic method of selectively neutralizing the biological activity of these hormones would provide an effective means of controlling or preventing the pathologic changes resulting from excessive hormone production.

The method of cancer therapy described in this invention has several advantages over present treatment methods. The method is non-invasive, selectively reversible, does not damage normal tissue, does not require frequent repeated treatments, does not cross the blood brain barrier and has reduced side effects.

The therapy may be selectively reversed by injecting the patient with a pharmaceutical composition comprising a neutralizing epitope molecule. This molecule should comprise the epitope sequence free of an immunogenic carrier. This non-immunogenic molecule will bind to the free antibodies previously induced against the epitope in the host.

DESCRIPTION OF THE INVENTION

Figure 1:
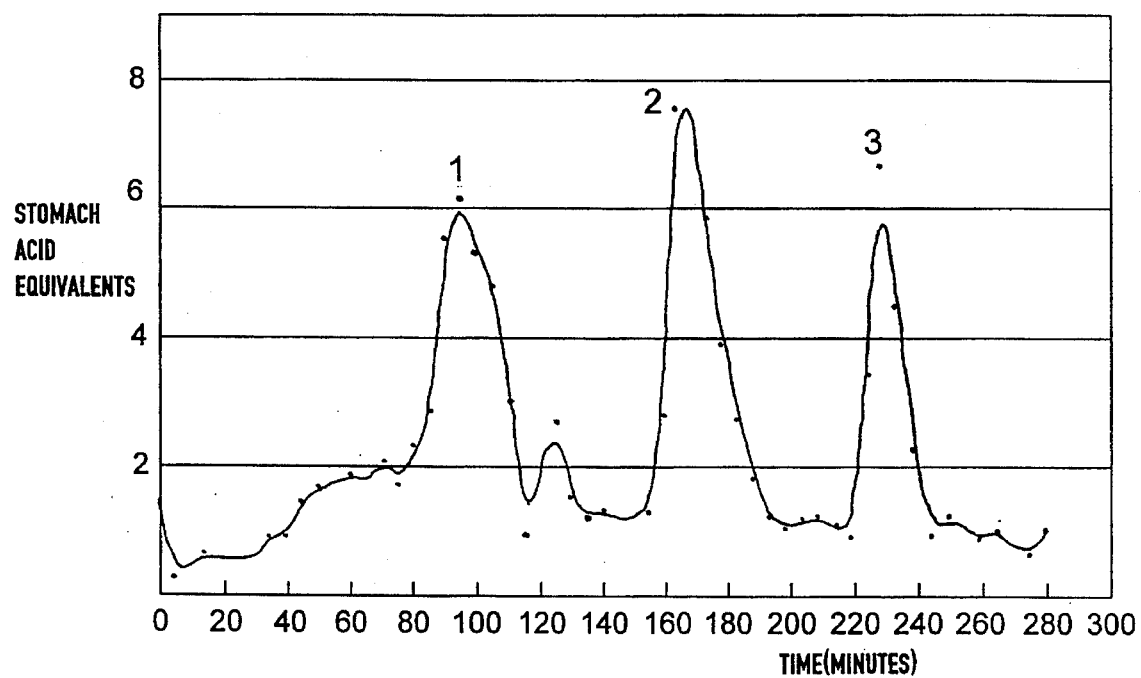
FIG. 1: illustrates the stomach acid secretions over time of a control rat injected sequentially with $hG_{17}$, antisera raised against an unrelated peptide and $hG_{17}$.

Since the different forms of gastrin vary in function, it is necessary to selectively neutralize specific forms of gastrin to control specific functions. To regulate gastrin-mediated secretion of stomach acid following meals (the principal source of excess stomach acid relating to ulcers), an immunogen must specifically target $G_{17}$. In order to selectively neutralize $G_{17}$, one or more antigenic epitopes on $G_{17}$ that are not found on $G_{34}$ or cholecystokinin which exhibits carboxy terminal homology with gastrin must be identified. As discussed above even though the C-terminus of $G_{17}$ and $G_{34}$ are identical the N-terminus of $G_{17}$ is very different from that of $G_{34}$. This results in antigenic epitopes that are unique to $G_{17}$ and can be separately targeted. We have identified and mapped such a unique epitope on $G_{17}$. A specific embodiment of the present invention concerns immunogens comprising this unique epitope. These immunogens result in high levels of anti-$G_{17}$ antibodies that do not crossreact with $G_{34}$ and block some or all of $G_{17}$ stimulation of gastric acid secretion while still allowing $G_{34}$ and CCK, which share with $G_{17}$ a common receptor, to carry out their physiologic function. The regulation of acid secretions can also involve the neutralization of $G_{34}$; we have also identified and mapped unique epitopes on $G_{34}$ that are not found on $G_{17}$ or CCK.

Our immunoneutralizing approach has several attractive advantages over current treatments for peptic ulcer. One of these advantages is the overcoming of the major problem of patient compliance since a daily dose of a drug is not required. This invention treats ulcers by preventing the release of excess stomach acid, unlike antacids that neutralize secreted acid. By administering our synthetic peptide as an immunogen, the frequency and quantity of treatment administration is decreased, while at the same time long-lasting control of acid production, long term prevention of recurrence, and reduced side effects and easier patient administration are provided. Unlike conventional anti-ulcer drugs, antibodies generated by the peptide immunogens are very specific to their target. They do not cross the blood-brain barrier, and their use avoids certain complications encountered with drugs, for example, liver toxicities associated with $H_2$ antagonists. In addition, unlike this invention, agonists or antagonists of $G_{17}$ have reduced efficency for controlling ulcers because such compounds have low specificity for the receptors for $G_{34}$ and CCK, which have identical receptor binding sites with $G_{17}$.

The immunogens against one form of gastrin, "little gastrin", or $G_{17}$, are constructed to produce an anti-gastrin immunogen component that will induce a selective and specific antibody response to $G_{17}$ in the immunized human or other vertebrate, but not to $G_{34}$ or CCK. This selective immunization to produce $G_{17}$ specific antibodies is crucial to avoid producing antibodies specific for or cross reactive with $G_{34}$, which might during the treatment of a specific condition induce undesirable side effects by blocking $G_{34}$ physiologic functions. The antibodies resulting from the immunization with such immunogens target the chemical structure of $G_{17}$ which is antigenically and immunogenically unique from the structure of $G_{34}$.

Peptides comprising the amino acid residues beginning from the amino terminus (amino acid residue number one) of $G_{17}$ and extending up to and including amino acid residue number 12 having the sequence pyro-Glu-Gly-Pro-Trp-Leu-Glu-Glu-Glu-Glu-Glu-Ala-Tyr, are used to prepare the immunogens of the invention by coupling them to an immunogenic carrier. For simplicity this sequence can be written based upon the international code for amino acids as pyro-E-G-P-W-L-E-E-E-E-E-A-Y. The immunogens may contain a part or all of this sequence. The last 5 carboxy-terminal end amino acids of the $G_{17}$ chemical structure (residues 13–17) are preferably not used, because this sequence is a common antigenic sequence between $G_{17}$, $G_{34}$, and at least one other hormone, cholecystokinin (CCK). Fragments, extensions, or other subsets of the natural hormone and of this 12 amino acid sequence of $G_{17}$ may be used.

The peptides which may be used to prepare the immunogens of the invention may comprise one of the following amino acid sequences: pGlu-Gly-Pro-Trp-Leu-Glu-Glu-Glu-Glu-Glu-Ala-Tyr-, pGlu-Gly-Pro-Trp-Leu-Glu-, pGlu-pGly-Pro-Trp-Leu-Glu-Glu-, pGlu-Gly-Pro-Trp-Leu-Glu-Glu-, pGlu-Gly-Pro-Trp-Leu-, PGlu-Gly-Pro-Trp-, pGlu-pGly-Pro-Trp-Leu-Glu-Glu-Glu-Glu-Ala-, pGlu-Gly-Pro-Trp-Leu-Glu-Glu-Glu-Glu-Glu-, pGlu-Gly-Pro-Trp-Leu-Glu-Glu-Glu-Glu.

The most preferred peptide used in the invention is the hexamer pGlu-Gly-Pro-Trp-Leu-Glu-. The other peptides such as pGlu-Gly-Pro-Trp-Leu-Glu-Glu-Glu-Glu-, pGlu-Gly-Pro-Trp-Leu-Glu-Glu-Glu-, pGlu-Gly-Pro-Trp-Leu- and pGlu-Gly-Pro-Trp are also preferred. One or more other amino acids may also be substituted for those of the natural sequence, so that increased or decreased binding capacity, specificity and/or titer of the antibody response against $G_{17}$ may be induced in the vaccinated host by the immunogen.

In other embodiments of the invention the use of preformed $G_{17}$ specific polyclonal and/or monoclonal antibodies and their derivatives or fragments produced by immunization, hybridoma, recombinant DNA or other technologies as a method of passive immunization for the control of gastric acid secretion stimulated by $G_{17}$ may be used.

The present invention also provides immunogens against a second form of gastrin, "big gastrin" or $G_{34}$. These immunogens are used to produce an anti-gastrin vaccine component that may be useful for the treatment or prevention of other gastrointestinal diseases and that will induce a selective and specific antibody response to $G_{34}$ (but not to $G_{17}$ or CCK) in the vaccinated human or other vertebrate. This selective immunization to produce $G_{34}$ specific antibodies is crucial to avoid producing antibodies specific for or cross reactive with $G_{17}$.

The $G_{34}$ immunogens specifically target chemical structures of $G_{34}$ which are antigenically and immunogenically unique from the structure of $G_{17}$. The chemical structures of $G_{34}$ utilized in this invention include, but are not limited to, peptides comprising the amino acid residues beginning from the amino terminus (amino acid residue number one) of $G_{34}$ and extending up to and including amino acid residue number 22. The sequence of this peptide is pyro-Glu-Leu-Gly-Pro-Gln-Gly-Pro-Pro-His-Leu-Val-Ala-Asp-Pro-Ser-Lys-Lys-Gln-Gly-Pro-Trp-Leu. Based upon the international code for amino acids, this sequence is pyro-E-L-G-P-Q-G-P-P-H-L-V-A-D-P-S-K-K-Q-G-P-W-L-. The $G_{34}$ immunogens may contain part or all of this sequence and comprise the sequence coupled to an immunogenic carrier. The sequence of the last 12 amino acids of the $G_{34}$ chemical structure (residues 23–34) are preferably not used in this invention because this sequence is a common antigenic sequence between $G_{17}$ and $G_{34}$. The sequence of amino acids are also not used since the sequence 29–34 has common antigenic sites with cholecystokinin. It is contemplated that the use of any fragments, extensions, or other subsets of the natural hormone and of this 22 amino acid sequence may be used as immunogens.

The most preferred peptide for use is the hexamer pGlu-Leu-Gly-Pro-Gln-Gly. The peptides pGlu-Leu-Gly-Pro-Gln-Gly-Pro-Pro-His- and pGlu-Leu-Gly-Pro-Gln-Gly-Arg-Pro-Pro-Pro-Pro-Cys are also preferred. One or more other amino acids may also be substituted and/or modified for those of the usual natural sequence, so that increased or decreased binding capacity, specificity and/or titer of the antibody response against $G_{34}$ may be induced in the vaccinated host by the immunogen.

Preformed $G_{34}$ specific monoclonal antibodies and their derivatives or fragments produced by hybridoma, recombinant DNA or other technologies may also be used as a method of passive immunization for the control of gastric acid secretion stimulated by $G_{34}$.

The peptides and immunogens may be produced by any process commonly used in the art including, for example, standard peptide synthesis technologies; methods employing recombinant DNA and associated technologies; antigen mimicking methods including antibody-internal image technology and any other related methodologies that produce a structure that immunologically resembles the antigenic structures of (mimotopes).

The means by which anti-gastrin antibodies prevent acid release has not been thoroughly established. Without being bound by theory, we believe that the acid suppressive effect of our immunogen is due to the binding of anti-gastrin antibodies to gastrin ($G_{17}$ and/or $G_{34}$) in the blood, and thereby preventing the binding of gastrin to its physiological receptors on the surfaces of parietal cells. Thus, gastrin is prevented from signaling parietal cells to secrete acid into the stomach.

For the $G_{17}$ and/or the $G_{34}$ epitopes of this invention to induce antibodies, it may be necessary to increase their immunogenicity by chemically coupling them to other molecules. Such molecules are termed "carriers". Any molecule capable of serving as a carrier may be used. Examples of carriers for this purpose include: diphtheria toxoid, tetanus toxoid, keyhole limpet hemocyanin, bovine serum albumin, etc. Fragments of these carriers, including single epitopes, may also be used. Any method of chemically coupling the epitopes to the carriers may be followed. A preferred method utilizes the bifunctional linking agent EMCS described in U.S. Pat. No. 4,302,386; Lee et al., 1981.

The epitopes can be alternatively rendered immunogenic by crosslinking (e.g., polymerizing) a number of epitopes. For this purpose, it may be necessary to extend the molecule bearing the $G_{17}$ or $G_{34}$ epitope by the addition of selected compounds that provide structures through which the crosslinking will occur. These additions must not disrupt the structure of the gastrin epitope, because the capacity to induce anti-gastrin antibodies would be lost. For example, to the carboxy terminal end of the $G_{17}$ epitope pyro-E-G-P-W-M-E-E is added the amino acid sequence K-R-P-P-P-P-K, to give pyro-E-G-P-W-M-E-E-K-R-P-P-P-P-K. This molecule is then polymerized with glutaraldehyde, which crosslinks the lysine(K)residues, to form the crosslinked immunogen. This crosslinked immunogen should induce specific antibodies against $G_{17}$.

It may be desirable in some applications to immunize against both $G_{17}$ and $G_{34}$. In this embodiment $G_{17}$ and $G_{34}$ immunogens are used in combination including optionally an immunogen with an epitope common to $G_{17}$ and $G_{34}$, e.g. Asp-Pro-Ser-Lys-Lys-Glu-Pro-Trp-Leu-, so that antibodies against both $G_{17}$ and $G_{34}$ are induced by the immunized host. The immunogens of this invention are therefore useful for more than just the treatment or prevention of ulcers. The immunogens may be used to treat any disease in which the gastrin stimulated secretion of stomach acid or stimulation of the growth of cancer by gastrin (e.g. colorectal and gastric) is a factor.

Administration of these immunogens, compositions containing them, or pharmaceutically acceptable and immunologically effective derivatives thereof, may be via any of the conventionally accepted modes of administration of agents which exhibit immunogenicity.

The compositions in which the immunogens are administered may be in a variety of forms. These include, for example, solid, semi-solid and liquid dosage forms, such as powders, liquid solutions or suspensions, suppositories, and injectable and infusible solutions. The preferred form depends on the intended mode of administration and therapeutic applications. The compositions also will preferably include conventional pharmaceutically acceptable carriers and may include other medicinal agents, carriers, adjuvants, excipients, etc., e.g., human serum albumin or plasma preparations. Preferably, the compositions of the invention are in the form of a unit dose. The amount of active compound administered as an immunization or as a medicament at one time, or over a period of time, will depend on the subject being treated, the manner and form of administration, and the judgment of the treating physician. However, an effective dose may be in the range of from about 1 ug to about 10 mg of the immunogen of this invention, preferably about 100 ug to about 2 mg; it being recognized that lower and higher doses may also be useful.

This invention provides a novel immunological approach to the treatment of tumors whose growth is dependent upon or stimulated by one or more of the forms of gastrin. According to the invention, antibodies are induced in the patient by passive or active immunization with immunogens that target one or more of the forms of gastrin. Such antibodies will bind to and neutralize the hormone to which the antibodies are directed, thereby preventing the hormone from acting upon the tumor. The antibody-mediated deprivation of hormonal activity thus constitutes a means of controlling gastrin dependent tumors.

This invention additionally provides a means of treatment for the effects of tumors that produce one or more forms of gastrin. In this embodiment, the immunogens of this invention are used to induce antibodies against the form of the hormone that is produced by the tumor. Such antibodies will bind to and neutralize the hormone, thereby preventing pathological consequences resulting from abnormally elevated levels of hormone.

This invention also provides a method for selectively reversing the antibody-mediated immunity induced by the anti-hormone immunogens of the invention. Soluble monovalent, monodeterminant epitopes are injected into the patient to bind to and neutralize the selected anti-hormone antibodies. The antibodies will then be incapable of binding additional quantities of hormone, and will no longer affect the hormone's biological activity.

The immunogens of this invention can be constructed to induce antibodies that specifically neutralize a single form of gastrin. This is advantageous in treating a tumor and pathologic condition, particularly one that is stimulated primarily or totally by a single form of gastrin. Alternatively, these specific immunogens can be selectively combined to produce an immunogen, in which the immunogen's individual constituents each induce antibodies that target distinct forms of gastrin. Combined immunogens would be used to treat tumors and conditions that are stimulated by more than one form of gastrin. Such an immunogen has the advantage of allowing for the addition or removal of individual immunogen constituents. The specificity of the antibody response can thus be controlled over time, thus enabling the physician to tailor the ongoing treatment to the needs of individual patients.

This example demonstrates a means of preparing immunogens to induce anti-$G_{47}$ or anti-$G_{34}$ antibody responses.

EXAMPLE 1

Peptides for the induction of specific immune responses to either $G_{17}$ or to $G_{34}$ were prepared by standard solid state synthesis methods. Each peptide was characterized as to amino acid content and purity.

Peptides with the following amino acid sequences were synthesized:

| | |
|---|---|
| Peptide 1- | Human $G_{17}$(1–6) ("h$G_{17}$(6)"): pGlu—Gly—Pro—Trp—Leu—Glu—Arg—Pro—Pro—Pro—Pro—Cys |
| Peptide 2- | Human $G_{17}$(1–5) ("h$G_{17}$(5)"): pGlu—Gly—Pro—Trp—Leu—Arg—Pro—Pro—Pro—Pro—Cys |
| Peptide 3- | Human $G_{17}$(1–4) ("h$G_{17}$(4)"): pGlu—Gly—Pro—Trp—Arg—Pro—Pro—Pro—Pro—Cys |
| Peptide 4- | Rat $G_{17}$(1–6) Leu 5 ("r$G_{17}$(6)Leu 5"): pGlu—Arg—Pro—Pro—Leu—Glu—Arg—Pro—Pro—Pro—Cys |
| Peptide 5- | Human $G_{34}$(1–6) ("h$G_{34}$(6)"): pGlu—Leu—Gly—Pro—Gln—Gly—Arg—Pro—Pro—Pro—Pro—Cys |
| Peptide 6- | Human $G_{34}$(13–22) ("h$G_{34}$/$G_{17}$ combination"): Asp—Pro—Ser—Lys—Lys—Gln—Gly—Pro—Trp—Leu—Pro—Pro—Pro—Pro—Cys |

Each of these peptides were conjugated to amino groups present on a carrier such as Diphtheria toxoid ("DT") via the terminal peptide cysteine residue utilizing hetero-bifunctional linking agents containing a succinimidyl ester at one end and maleimide at the other end of the linking agent.

To accomplish the linkage between any of Peptides 1–6 above and the carrier, the dry peptide was dissolved in 0.1M Sodium Phosphate Buffer, pH 8.0, with a thirty molar excess of dithiothreitol ("DTT"). The solution was stirred under a water saturated nitrogen gas atmosphere for four hours. The peptide containing reduced cysteine was separated from the other components by chromatography over a G10 Sephadex column equilibrated with 0.2M Acetic acid. The peptide was lyophilized and stored under vacuum until used. The carrier was activated by treatment with the hetero-bifunctional linking agent e.g. Epsilon-maleimidocaproic acid N-hydroxysuccinimide ester, ("EMCS"), in proportions sufficient to achieve activation of approximately 25 free amino groups per $10^5$ molecular weight of carrier. In the specific instance of diphtheria toxoid, this amounted to the addition of 6.18 mg of EMCS (purity 75%) to each 20 mg of diphtheria toxoid.

Activation of diphtheria toxoid was accomplished by dissolving each 20 mg aliquot of diphtheria toxoid in 1 ml of 0.2M Sodium Phosphate Buffer, pH 6.45. Aliquots of 6.18 mg EMCS were dissolved into 0.2 ml of Dimethyl Formamide ("DMF"). Under darkened conditions, the EMCS was added dropwise in 50 microliter ("ul") amounts to the DT with stirring. After 2 hours of incubation in darkness, the mixture was chromatographed on a G50 Sephadex column equilibrated with 0.1M Sodium Citrate buffer, pH 6.0, containing 0.1 mM EDTA.

Fractions containing the EMCS activated diphtheria toxoid were concentrated over a PM 10 ultrafiltration membrane under conditions of darkness. The protein content of the concentrate was determined by either the Lowry or Bradford methods. The EMCS content of the carrier was determined by incubation of the activated carrier with cysteine-HCl followed by reaction with 10 mM of Elman's Reagent 5,5'dithio-bis (2-nitrobenzoic acid) 10 mM. The optical density difference between a blank tube containing cysteine-HCl and the sample tube containing cysteine-HCl and carrier was translated into EMCS group content by using the molar extinction coefficient of $13.6 \times 10^3$ for 5-thio-2-nitro benzoic acid at 412 nm.

The reduced cysteine content (—SH) of the peptide was also determined utilizing Elman's Reagent. Approximately 1 mg of peptide was dissolved in 1 ml of nitrogen gas-saturated water and a 0.1 ml aliquot of this solution was reacted with Elman's Reagent. Utilizing the molar extinction coefficient of 5-thio-2-nitro-benzoic acid ($13.6 \times 10^3$), the free cysteine —SH was calculated. An amount of peptide containing sufficient free —SH to react with each of the 25 EMCS activated amino groups on the carrier was dissolved in 0.1M Sodium Citrate Buffer, pH 6.0, containing 0.1 mM EDTA, and added dropwise to the EMCS activated carrier under darkened conditions. After all the peptide solution had been added to the carrier, the mixture was incubated overnight in the dark under a water saturated nitrogen gas atmosphere.

The conjugate of the peptide linked to the carrier via EMCS is separated from other components of the mixture by chromatography over a G50 Sephadex column equilibrated with 0.2M Ammonium Bicarbonate. The conjugate eluted in the column void volume is lyophilized and stored desiccated at $-20°$ C. until used.

The conjugate may be characterized as to peptide content by a number of methods known to those skilled in the art including weight gain, amino acid analysis, etc. Conjugates of Peptides 1–6 and diphtheria toxoid produced by these methods were determined to have 20–25 moles of peptide per $10^5$ MW of carrier and all were considered suitable as immunogens for immunization of test animals.

EXAMPLE 2

As examples of the utilization of peptides containing sequences of human gastrin as immunogens to induce immune responses against $hG_{17}$ or $hG_{34}$, we have immunized rats with the conjugate immunogens constructed from Peptides 1–6 of Example 1 and Diphtheria toxoid ("DT") (referred to as Immunogens 1–6, respectively).

Six different groups of 15 Sprague-Dawley female rats (200 gm. body weight) were each immunized with one of the immunogens constructed from Peptides 1–6. Each animal was injected subcutaneously with 0.25 ml of immunogen consisting of 0.1 mg of conjugate dissolved in 0.125 ml of 0.1M Sodium Phosphate Buffered Saline, pH 7.3, emulsified with an equal volume of Squalene-Arlacel (4:1 ratio volume/volume) vehicle containing 0.05 mg of Nor MDP as adjuvant.

Two additional groups of 15 rats were immunized with a peptide-DT conjugate in which the peptide had no sequence homology with gastrins so as to act as a negative immunization control.

Each rat was given an injection of immunogen at 0, 3, and 6 weeks. Blood was collected from each rat at 3, 6, and 8 weeks of the experiment. Serum was collected from each blood sample and stored at $-20°$ C. until utilized in assays to determine the presence of anti-gastrin antibodies.

Two types of assays were used to detect anti-gastrin antibodies. A solid-phase enzyme linked immunosorbent assay (ELISA) and a liquid phase radioimmunoassay (RIA) were employed.

ELISA was used to screen for reaction or cross reaction of antisera raised against Peptides 1–6 with Peptides 1–6 or with $hG_{17}$, $hG_{34}$, or hCCK. The RIA was used to quantitate the antibody levels in the antiserum of each immunized animal that was reacted with $hG_{17}$ or $hG_{34}$ by determining the antigen binding capacity (ABC), expressed as pg hormone bound per ("ul") of antiserum (pg/ul).

The ELISA was conducted by coating polystyrene 96 well plates (Immulon II) with 1 ug/ml of Peptides 1–6, $hG_{17}$, hG34, or hCCK antigen. Serial dilutions of test antisera of $1 \times 10^{-1}$ to $1 \times 10^{-8}$ were incubated with each test peptide for 30 minutes at room temperature. In some instances antisera raised against a particular peptide of the Peptides 1–6 were preincubated with large excesses of the other peptides of the Peptide 1–6 group or with $hG_{17}$ or $hG_{34}$ in an attempt to inhibit binding of the antiserum to its particular peptide and also to demonstrate the occurrence of antibodies in the antisera that were specific for the sequence (spacer) of each peptide that was common to all of Peptides 1–6 (e.g. Arg-Pro-Pro-Pro-Pro-Cys). After washing each well thoroughly to remove unbound antibody, each well was treated with biotinylated anti-rat immunoglobulin reagent for 30 minutes at room temperature. After another wash sequence to remove unbound anti-rat reagent, avidin-alkaline phosphatase conjugate was added and the mixture was incubated for an additional 30 minutes. The mixture was washed thoroughly to remove unbound avidin-alkaline phosphatase reagent, and the chromogenic substrate PNPP was added for a 10 minute period. The absorbance of each well was read at 490 nm after the 10 minute incubation.

The standard RIA procedure was followed. In the RIA, 0.1, 1.0 or 10.0 ul aliquots of antiserum were incubated with approximately 200 pg of $^{125}$I labeled $hG_{17}$ or 400 pg of labeled hG34. The antisera were incubated with label for 2 hours, and were followed by a precipitation of hormone-antibody complexes with 25% polyethylene glycol. Antigen binding capacities for each antiserum where then determined from the amount of radioactive hormone precipitated. To demonstrate the specificity of the reaction of the $^{125}$I labeled hormone with the antisera, aliquots of the antisera were preincubated in some tests with excess amounts of the hormone that were not labeled with $^{125}$I to inhibit binding of the antisera to the labeled hormone.

The specificities of the antibody responses induced by Immunogens 1–6 as measured by ELISA are depicted in Table 1. Immunogen 1, containing the peptide sequence of $hG_{17}$ (1–6), induced antibodies that reacted strongly with $hG_{17}$ and $hG_{17}$ (1–6) peptide, but only weakly with $hG_{34}$ (1–6) or $hG_{34}$ (13–22). Antisera raised to Immunogen 1 did not react with $hG_{34}$. Inhibition experiments with Peptides 1–6 demonstrated that the weak reactivity of anti-Immunogen 1 antibodies with $hG_{34}$ (1–6) and $G_{34}$ (13–22) peptides was due to the presence of antibodies that were induced by the spacer sequence (-Arg-Pro-Pro-Pro-Cys) common to all the peptide sequences of Immunogens 1–6.

Immunogens 2 and 3 induced antibody responses specific for $hG_{17}$ that were much weaker than those induced by Immunogen 1 (Table 1). Inhibition experiments, demonstrated that the weak reactivities of anti-Imunogen 2 and 3 antibodies for Peptides 1–6 are specific for the common spacer sequence of Peptides 1–6.

Immunogen 4, containing the rat $G_{17}$ sequence, induced antibodies that weakly reacted with Peptides 1–6, but not $hG_{17}$ or $hG_{34}$ (Table 1). Inhibition experiments demonstrated that these antibodies were directed against the spacer sequence common to Peptide 1–6.

Immunogen 5 $hG_{34}$ (1–6), induced antibodies that strongly reacted with $hG_{34}$ and Peptide 5, $hG_{34}$ (1–6), but weakly with the other peptides and not at all with $G_{17}$. Inhibition experiments demonstrated that the reactivity with Peptides 1–4 and 6 was due to anti-spacer specific antibodies.

Immunogen 6, $hG_{34}$ (13–22), induced antibodies that reacted weakly with Peptides 1–6, but not with $hG_{17}$.

Inhibition experiments demonstrated that the antibodies binding Peptides 1–6 were specific for the common spacer sequence.

TABLE 1

| Antisera to: | $hG_{17}$ | Peptide 1 $hG_{17}(1-6)$ | Peptide 2 $hG_{17}(1-5)$ | Peptide 3 $hG_{17}(1-4)$ | Peptide 4 $rG_{17}(1-6)$ | Peptide 5 $hG_{34}(1-6)$ | Peptide 6 $hG_{34}(13-22)$ | $HG_{34}$ |
|---|---|---|---|---|---|---|---|---|
| Immunogen 1 | ++ | +++ | + | + | + | + | + | 0 |
| $hG_{17}(1-6)$-DT | | | – | – | – | – | – | |
| Immunogen 2 | + | + | + | + | + | + | + | 0 |
| $hG_{17}(1-5)$-DT | | – | | – | – | – | – | |
| Immunogen 3 | + | + | + | + | + | + | + | 0 |
| $hG_{17}(1-4)$-DT | – | – | – | | – | – | – | |
| Immunogen 4 | 0 | + | + | + | + | + | + | 0 |
| $rG_{17}(1-6)$-DT | | – | – | – | | – | – | |
| Immunogen 5 | 0 | + | + | + | + | ++ | + | +++ |
| $hG_{34}(1-6)$-DT | | – | – | – | – | | – | |
| Immunogen 6 | + | + | + | + | + | + | + | + |
| $hG_{34}(13-22)$-DT | | – | – | – | – | – | – | – |

+++ to +: Strongly reactive
+: Weekly reactive
0: No reaction

All antisera were also tested against hCCk; none of the antisera bound to hCCK.

Table 2 demonstrates the RIA-measured antigen binding capacities ("ABC") versus $hG_{17}$ or $hG_{34}$ of antisera raised against Immunogens 1–6 after three immunizations of rats with 0.1 mg of conjugate.

TABLE 2

| | Mean RIA ABC (pg/ul) | |
|---|---|---|
| Rats Immunized With: | $hG_{17}$ | $hG_{34}$ |
| Immunogen 1 $hG_{17}(1-6)$-DT | 19.29 | 0.00 |
| Immunogen 2 $hG_{17}(1-5)$-DT | 7.59 | 0.00 |
| Immunogen 3 $hG_{17}(1-4)$-DT | 2.15 | 0.00 |
| Immunogen 4 $rG_{17}(1-6)$-DT | 0.00 | 0.00 |
| Immunogen 5 $hG_{34}(1-6)$-DT | 0.00 | 6.38 |
| Immunogen 6 $hG_{34}(13-22)$ | 0.00 | 1.28 |

The liquid phase RIA demonstrated that Immunogens 1–3 containing the $hG_{17}$ peptide sequence induced antibodies that reacted only with $hG_{17}$ and that Immunogen 5 containing the $hG_{34}$ sequence, induced antibodies that reacted only with $G_{34}$. Immunogen 6 induced very low ABC's to $G_{34}$.

The ELISA and RIA assays thus demonstrate the specificity of the responses to $hG_{17}$ or $hG_{34}$ that are induced by Immunogens 1–6.

EXAMPLE 3

This example demonstrates the ability of antisera raised against Peptide 1 ($hG_{17}$ (1–6)) to neutralize the in vivo acid stimulating activity of $hG_{17}$. In this demonstration an amount of $hG_{17}$ is mixed with an excess amount of anti-Peptide 1 antiserum sufficient to bind to all the $hG_{17}$ prior to injection of the complex into a normal (non-immunized) rat.

In control experiments the amount of $hG_{17}$ sufficient to stimulate an increase of acid secretion of at least 100% above nonstimulated acid secretion in normal rats was determined to be 0.4 ug of $hG_{17}$ hormone per kg body weight.

Antisera from the rats immunized with Immunogen 1 were pooled and standard amounts of antisera were incubated with 200 pg $^{125}I$ labeled $hG_{17}$ after incubation with increasing amounts of cold hG17 as inhibitor. Based on this inhibition study 1 ml of antiserum was capable of binding 1000× the 0.4 ug/kg dose of $hG_{17}$ to be administered to rats. As a safety factor, the 0.4 ug/kg (approximately 120 ng) of hormone was mixed with 2.5 ml of anti-$hG_{17}$ specific antiserum raised against Immunogen 1.

Rats to be injected with $hG_{17}$ complexed with anti-hG17 antibodies were surgically prepared for collection of stomach secretions by the perfused rat stomach procedure.

Under general anesthesia and following tracheostomy, the rat was cannulated via the esophagus and duodenum to allow continuous perfusion of the stomach with 0.9% saline. The stomach perfusate was collected as 5 minute interval samples and was titrated for acid content by neutralization with base (sodium hydroxide). Incremental and total acid input during the duration of the experiment and after each treatment was determined.

Each control or experimental test rat was first injected with 0.4 ug/kg $hG_{17}$ to determine the rats total acid secretory response to this treatment. The first treatment was followed one hour later in test rats with an injection of 0.4 ug/kg of $hG_{17}$ that had been premixed for one hour with 2.5 ml of anti-$hG_{17}$ specific antiserum. Control rats received an injection of $hG_{17}$ mixed with 2.5 ml of antiserum raised against an unrelated peptide. After one hour, a second injection of free $hG_{17}$ was administered to the test and control rats; and stomach perfusate was collected for an additional hour. The total acid output induced by the second and third injections of $hG_{17}$ were expressed as a percentage of the total acid output induced by the first injection of $hG_{17}$.

Figure 2:
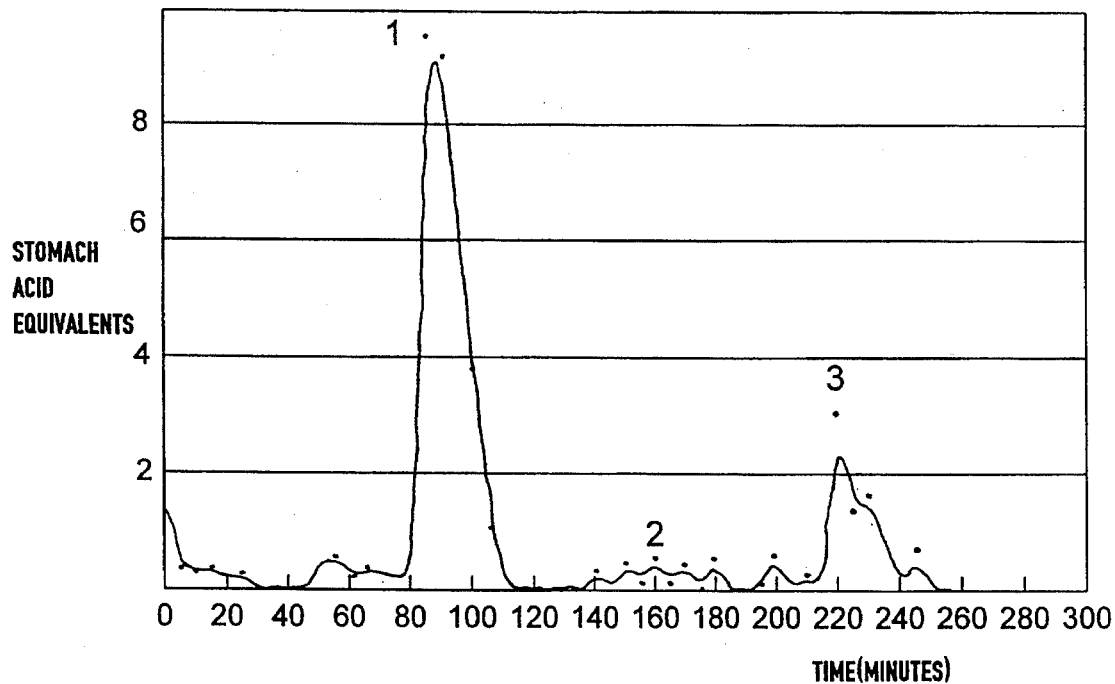
FIG. 2: illustrates the stomach acid secretion over time or a rat injected sequentially with $hG_{17}$, $hG_{17}$ premixed with anti $hG_{17}$ antisera; and $hG_{17}$.

In five rats tested by this experimental procedure there was an 81%–100% (mean=94%) reduction in the acid secreted by the perfused rat stomach in response to the hormone premixed with anti-$hG_{17}$ specific antibody (second injection) or to the third injection consisting of free $hG_{17}$ alone. Control rats experienced little or no reduction in acid secretion stimulated by the second and third injections of hormone. FIG. 1 and FIG. 2 illustrate the responses of a control rat (FIG. 1) and experimental rat (FIG. 2) to these treatments.

EXAMPLE 4

A major application of this invention is the active immunization of humans to induce specific immunity against $G_{17}$ for ulcer therapy and prevention. In this example, it is demonstrated that active immunization with an anti-$G_{17}$ immunogen induces antibodies that dramatically suppress $G_{17}$ mediated release of stomach acid.

To actively immunize rats against $G_{17}$, we follow the methods used to obtain antisera in the passive immunization tests as described in Example 3. An immunogen consisting of the $G_{17}(6)$ peptide covalently coupled to Diphtheria toxoid (DT) is prepared as described in Example 1. This immunogen is suspended in Phosphate Buffered Saline at a concentration of 4.0 mg/ml. The antigen is emulsified in squalene:arlacel (4:1) vehicle, at a final ratio of 1:1 (antigen:vehicle). Nor-MDP is included in the mixture to give a final concentration of nor-MDP of 200 ug/ml. The final concentration of the DT-$G_{17}(6)$ in the formulation is 2.0 mg/ml. Experimental rats are injected with 0.25 ml of this preparation intraperitoneally. Each injection thus delivers approximately 500 ug of immunogen plus 50 ug of nor-MDP. A second injection is similarly administered 21 days later.

Blood samples for antibody analysis are obtained by tail vein bleeding before the first injection and 14 days after each injection. Sera is prepared by allowing the blood to clot for 30 minutes at room temperature followed by centrifugation at 400×g to remove the clots. The Sera are stored frozen until used.

To determine the antibody responses of the immunized rats, a RIA is employed as described in Example 2. The results of this test show that the immunization procedure induces high titers of antibody against $G_{17}$. These responses are specific for $G_{17}$; no reactivity is detected with $G_{34}$, with pentagastrin (the biologically active, carboxy terminal fragment of $G_{17}$, $G_{34}$, and CCK), or with CCK. The antibodies are thus directed against the unique epitope on $G_{17}$ that is selectively targeted by the immunogen. These results are similar to those of Example 2.

The use of the immunogens described herein for the active immunogen is not limited to the adjuvant, vehicle, injection schedule, etc., described above. Any means of safely inducing immunity against $G_{17}$ using the immunogens described can be applied. This includes using alternative dosages, routes, vehicles, adjuvants, exipients, slow-release compounds, etc.

We test for the neutralization of $G_{17}$'s biological activity in the immunized animals using the perfused rat stomach method, as described in Example 3, with the important difference that we do not inject antisera into the rats (passive immunization) because the actively immunized rats are making their own antibodies against $G_{17}$. The dosages of compounds administered in these tests, with delivery times of 5 minutes per total dose, are: $G_{17}$=0.4 ug/kg, $G_{34}$=0.8 ug/kg, and pentagastrin=2.0 ug/kg. Stomach contents sampling times are 5 minutes per sample. The stomach acid outputs are calculated as the percent of maximal acid output $$= (100) \frac{An - Ab}{Amax - Ab},$$

where An=the acid produced over each 5 minute sampling interval (as determined by titration with NaOH); Amax=the maximal 5 minute release of stomach acid upon stimulation, usually (but not necessarily) by pentagastrin; and Ab=the baseline level of acid present at the time of a given stimulation (with $G_{17}$, pentagastrin, or $G_{34}$).

Figure 3:
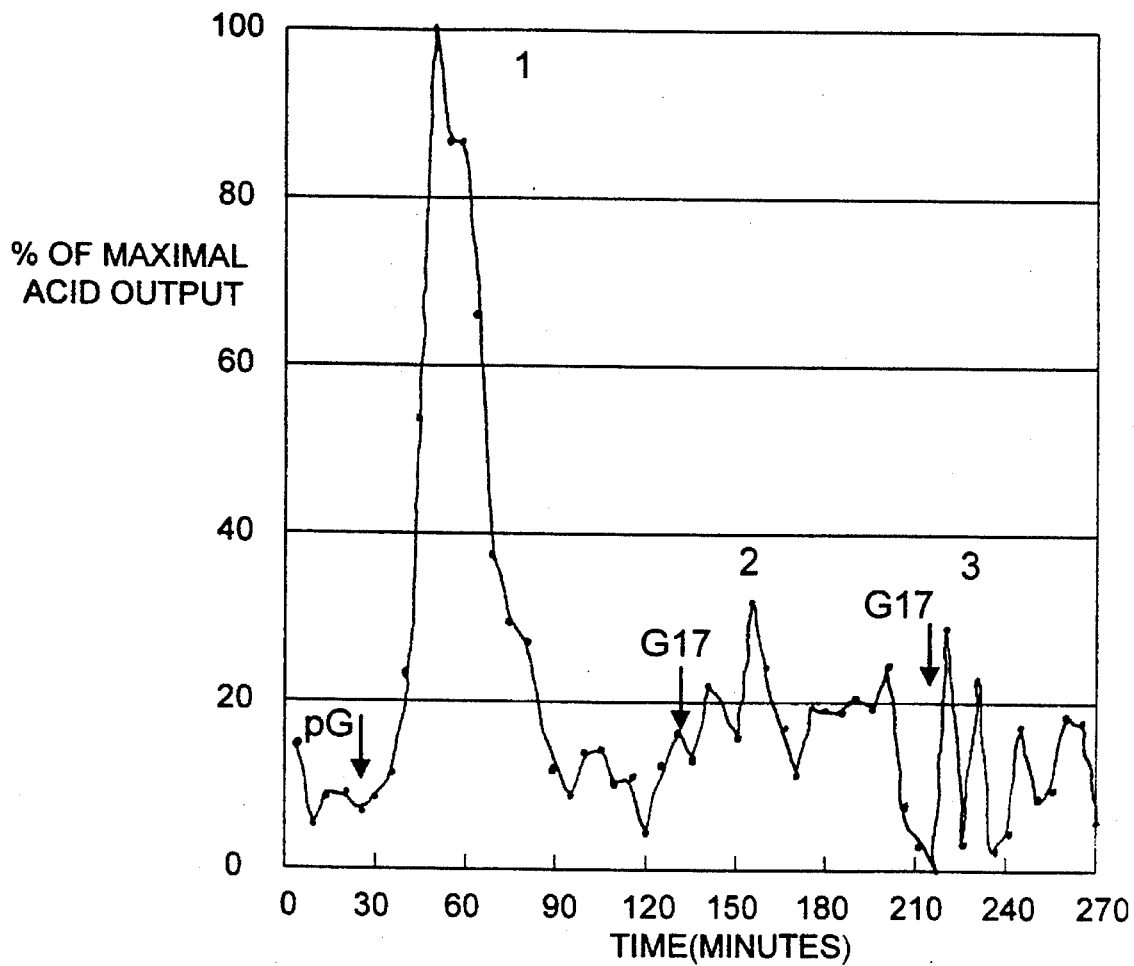
FIG. 3: illustrates the stomach acid output over time in a rat actively immunized against $G_{17}$ in response to an injection of pentagastrin ("pG") followed by injections of $G_{17}$.
Figure 4:
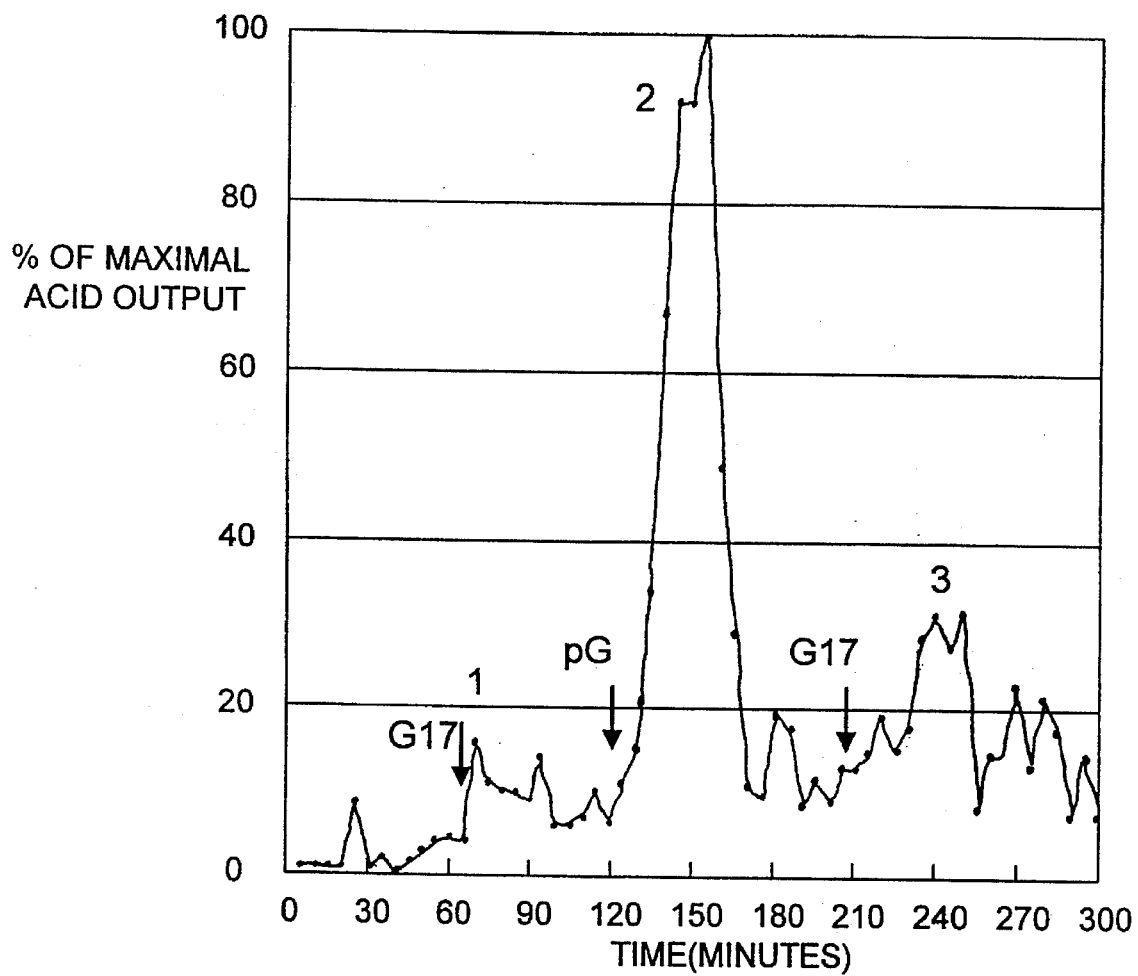
FIG. 4: illustrates the stomach acid output over time in a rat actively immunized against $G_{17}$ in response to an injection of $G_{17}$ followed by injections of pentagastrin and $G_{17}$.

The effects of active immunization against $G_{17}$ upon the $G_{17}$ and pentagastrin ("pG") induced acid secretion are shown in FIGS. 3 and 4. The ordinate represents the percent of acid output compared to the maximal acid output induced by pentagastrin. These experiments differed, by design, in the order of $G_{17}$ and pentagastrin challenge. In both cases, it is clear that in the $G_{17}$ immunized rats the production of stomach acid in response to $G_{17}$ (FIG. 3, Peaks 2 and 3; FIG. 4, Peaks 1 and 3) is substantially reduced in comparison with acid secretion induced by pentagastrin (FIG. 3, Peak 1; FIG. 4, Peak 2). The mean reduction in the total $G_{17}$ mediated acid secretion in our $G_{17}$ immune rats is 85% (compared to pentagastrin).

Figure 5:
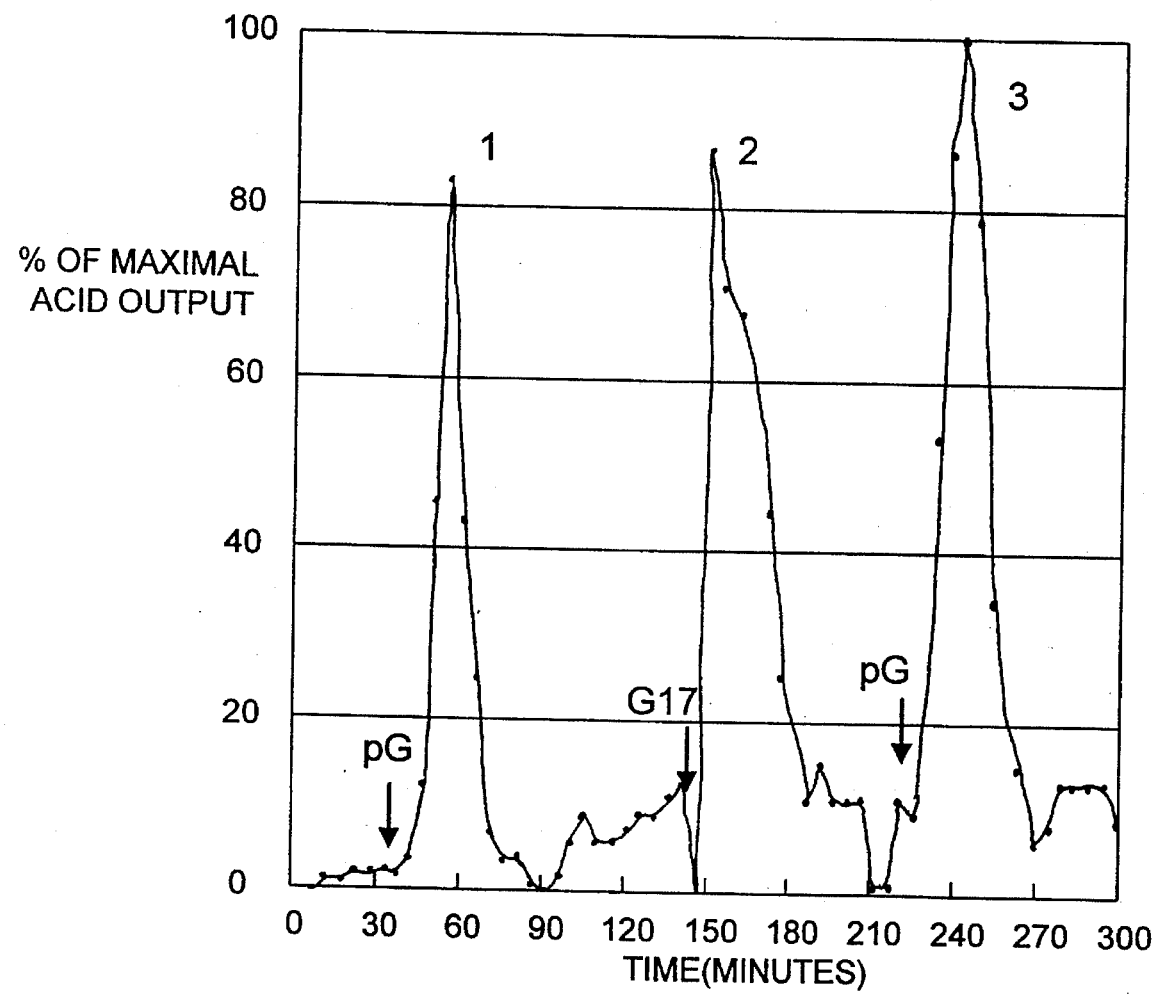
FIG. 5: illustrates the stomach acid output over time in a control rat in response to the sequential injection of pG, $G_{17}$ and pG.

We verified that the acid reductions were a direct consequence of immunization against $G_{17}$ by conducting challenges with $G_{17}$ or pentagastrin in control rats. The control animals were immunized in an identical manner as the $G_{17}$-immune rats, except that the controls received antigen consisting of DT conjugated to an unrelated peptide (i.e., non-crossreactive with gastrin). RIAs and ELISAs, run on sera from these animals, demonstrated that they produced high antibody titers against both DT and the unrelated peptide, but none against $G_{17}$, pentagastrin, $G_{34}$ or CCK. When tested for acid secretion, the control rats responded equally well to challenges with both $G_{17}$ and pentagastrin. The results of such a test are shown in FIG. 5. This rules out the remote possibility that the neutralization of G17 in the $G_{17}$-immune rats was caused by non-specific factors (e.g., adjuvant effects, crossreactive anti-DT antibodies, etc.).

A technical challenge presented by the perfused rat stomach assay was the selection of the appropriate acid stimulatory compound for use as a positive control. The exquisite specificity for $G_{17}$'s unique epitope that is characteristic of antibodies induced by our immunogen enabled us to use the ideal control compound: pentagastrin. Pentagastrin comprises the receptor binding/stimulatory sequence of $G_{17}$ and also of both $G_{34}$ and CCK, and it is not bound by antibodies induced by our immunogen. The responses to pentagastrin demonstrated that our immunized animals' acid response mechanism to $G_{17}$ stimulation were functional. In addition, the pentagastrin responses established the level of acid secretion to be expected from $G_{17}$ stimulation. The dosages of $G_{17}$ and pentagastrin, which we determined experimentally, were selected to induce approximately equal acid secretory responses in control rats (see FIG. 5). Thus, we were able to accurately quantitate reductions in acid secretion resulting from the neutralization of $G_{17}$.

Figure 6:
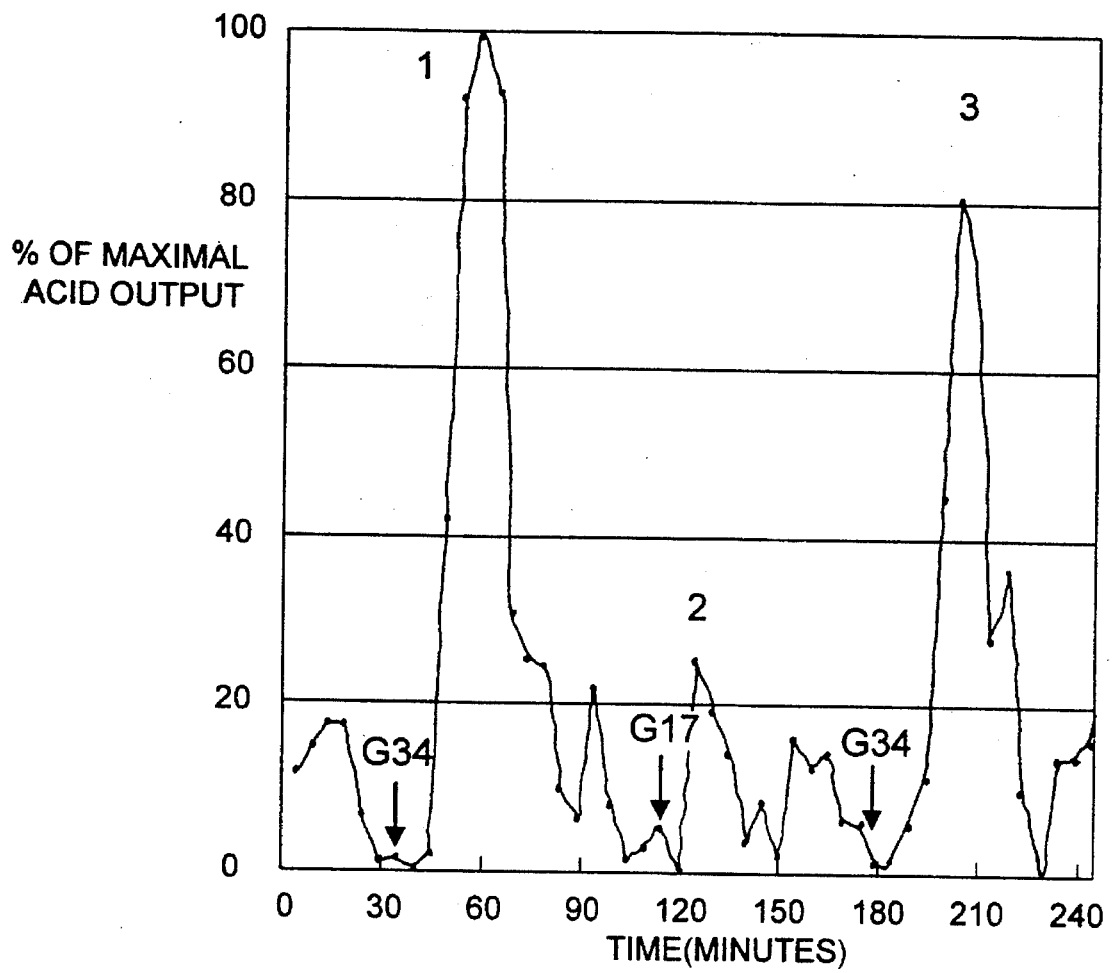
FIG. 6: illustrates stomach acid output over time in a rat actively immunized against $G_{17}$ in response to sequential injections of $G_{34}$, $G_{17}$ and $G_{34}$.
Figure 7:
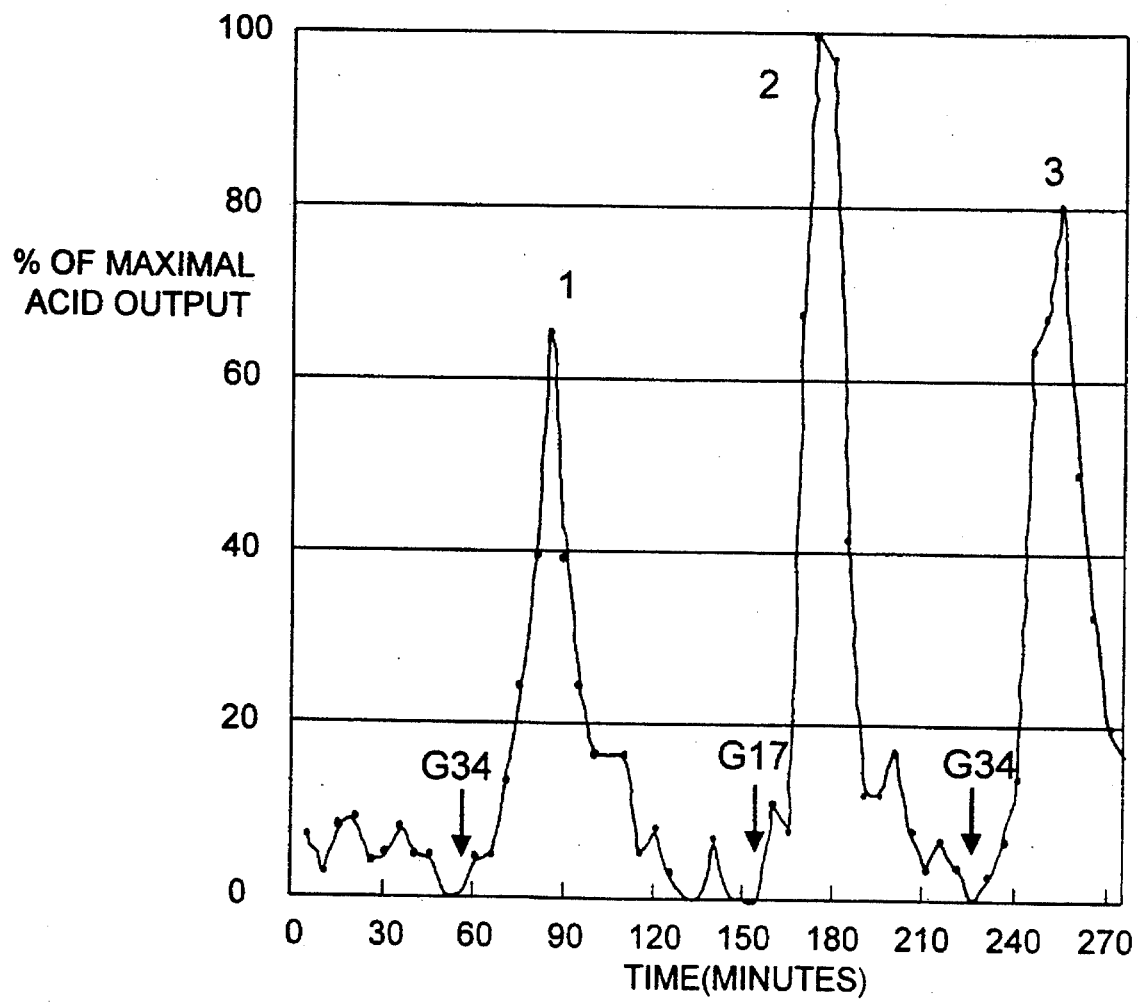
FIG. 7: illustrates stomach acid output over time in a control rat in response to sequential injections of $G_{34}$, $G_{17}$ and $G_{34}$.

For completeness, we have also challenged with $G_{34}$. We designed our immunogen to specifically neutralize $G_{17}$ mediated acid secretion (particularly following food intake) and to have no effect upon acid output induced by $G_{34}$ (which provides for basal stomach activity). Since the antisera from the $G_{17}$ immune rats do not react with $G_{34}$, we expected to see no effect upon $G_{34}$'s ability to stimulate acid secretion. Indeed, as shown in FIG. 6, the immunized rats secreted normal quantities of acid in response to $G_{34}$ stimulation (Peaks 1 and 3). As expected, the injection of $G_{17}$ failed to induce acid secretion in these animals (FIG. 6, Peak 2). Both $G_{17}$ and $G_{34}$ induce strong acid secretory responses in control rats (immunized against an irrelevant peptide), as can be seen in FIG. 7. Clearly, the anti-$G_{17}$ antibodies induced by our immunogen have no effect upon the functions of other molecules to which the antibodies do not bind. The $G_{17}(6)$ based immunogen described herein induces antibodies that are specific for $G_{17}$ and neutralize $G_{17}$'s acid releasing activity. Such an immunogen should thus protect against and cure peptic ulcers.

EXAMPLE 5

This example demonstrated that a polymerised peptide immunogen can be constructed and used to reduce anti-$G_{17}$ antibody responses. Synthetic peptides have been produced that contain the unique epitope on $G_{17}$ and in addition carry reactive groups that can be selectively bound to crosslinking agents. These peptides serve as monomers in the construction of a polymer immunogen. By including two or more reactive groups in each peptide it is possible to construct multi-peptide aggregates, or polymers, by reaction of the groups with a cross-linking agent. Such polymers are then used as immunogens to induce antibodies against the $G_{17}$ epitope expressed by the peptide. These antibodies bind to $G_{17}$ in vivo and neutralize $G_{17}$, thus mediating an anti-ulcer effect. These polymerized peptides have an advantage in that they can be used as immunogens by themselves without a coupling to an immunogenic carrier.

The following peptide designated as Peptide 7 was constructed:

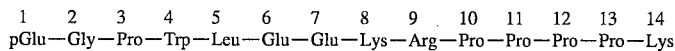

pGlu—Gly—Pro—Trp—Leu—Glu—Glu—Lys—Arg—Pro—Pro—Pro—Pro—Lys

The $G_{17}$ epitope is contained in amino acids 1–7 of the peptide. Other epitopes eg. $G_{34}$ epitopes, can also be used to construct other polymer immunogens according to the invention. Amino acids 8 and 14, which are both Lys, contain amino groups as side groups. These amino groups act as functional groups which are reacted with the functional groups on the crosslinking agent to form the crosslinked peptide polymer. Other amino acids containing side functional groups could be substituted for Lys depending on the reactivity of the functional group with the group on the crosslinking agent to be used. The location of the functional amino acids can be varied in the peptide as long as they are not positioned within the epitope region. Additional reactive amino acids could also be added to increase crosslinking. These additional amino acids could be reactive with the same or alternative crosslinking agents. It follows that more than one type of crosslinking agent can be used.

Amino acids 9–13 comprise a "spacer region" between the reactive amino acids 8 and 14. The composition, number of amino acids and length of the spacer can be varied. If desirable, helper T-cell epitopes can also be included in the peptide.

Peptide 8 was synthesized and purified by standard solid phase peptide synthesis and purification methodologies. Any other method of peptide production well known to those skilled in the art including recombinant DNA technology can also be used to produce the peptides of the invention.

5.0 mg of the peptide was dissolved in 1.0 ml phosphate buffer (0.1M; pH=6.8). To this was added glutaraldehyde (Grade 1, Sigma Chemical Co.) in a 2:1 molar ratio of glutaraldehyde to peptide. The glutaraldehyde was added dropwise with stirring, at room temperature.

The reaction was allowed to proceed overnight, at room temperature, with stirring. 50.0 mgs. of sodium borohydride were then added slowly to the reaction mixture, and the mixture was stirred at room temperature for an additional hour. The mixture was transferred to dialysis tubing, 1,000 molecular weight cutoff (#132636, Spectrum Medical Industries, Inc.), and exhaustively dialyzed against saline. The peptide-polymer was stored frozen at –20° C.

The polymer was analyzed by SDS-PAGE using a 15% polyacrylamide gel. The electrophoresis demonstrated that the polymerized peptide contained polymers of various sizes comprising multiples of the peptide. The average polymer contained 6 peptides, however; the size of the polymers ranged up to 12 peptides per molecule.

A second polymer was made using the identical procedures, except that a 20:1 molar ratio of glutaraldehyde to peptide was used. The SDS-PAGE analysis of the second polymer similar results with respect to the size range as compared to the 2:1 polymer.

Figure 8:
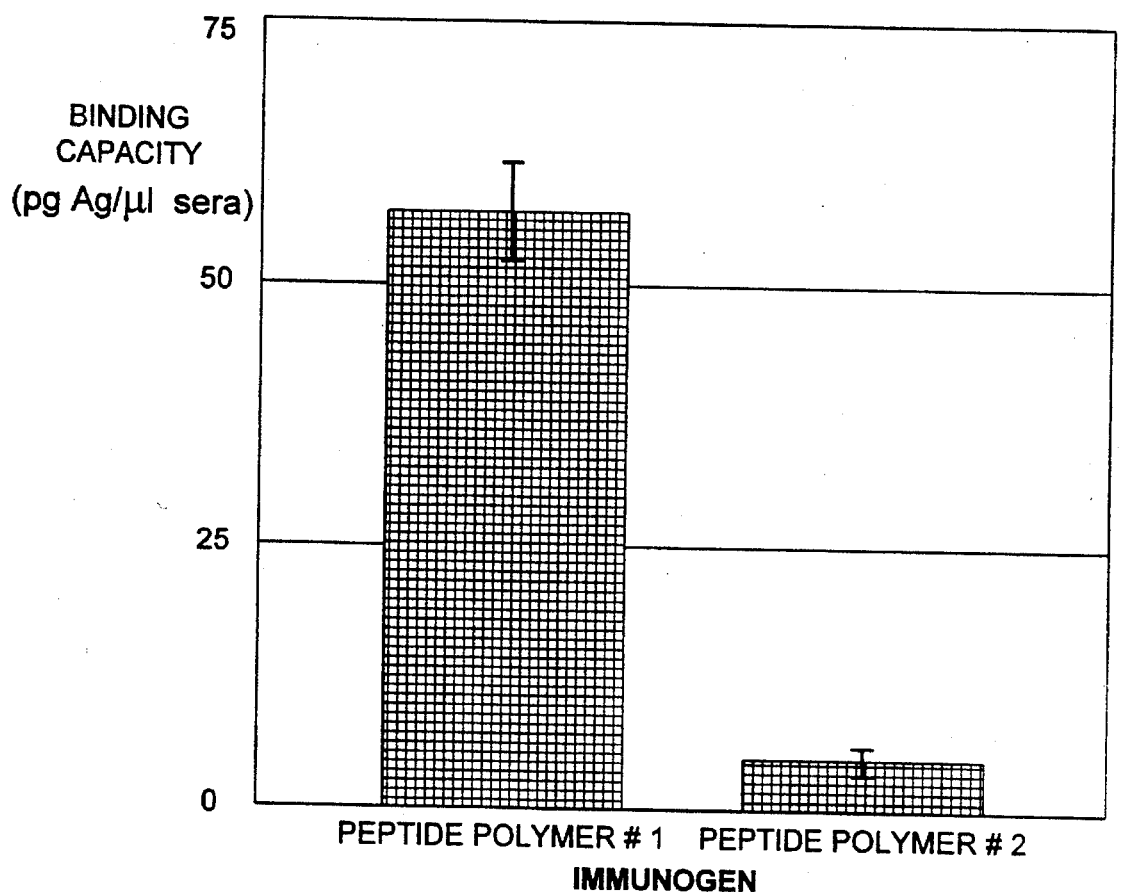
FIG. 8: depicts the binding capacity in picograms ("pg.") of Antigen per microliter ("ul") of sera of anti-$G_{17}$ antibodies induced by two synthetic peptide antigen epitope polymers of the invention.

Each polymer preparation, 2:1 and 20:1, was used to immunize two separate groups of five mice per group. Prior to injecting the mice with polymer, blood samples were taken from each mouse. The preparation was suspended in Freunds Complete Adjuvant ("FCA") H37Ra (DIFCO Labs) in a 1:1 (vol:vol) ratio of polymer:FCA. The mice were each injected intraperitoneally with 100 ug polymer in 0.2 ml of the mixture. After 21 days each mouse was given a second injection of the same polymer with which it had been injected previously. In the second injection, the antigen was administered intraperitoneally in saline, at 100 ug per mouse. Each mouse was bled 14 days after the second injection and the sera were isolated. The mouse sera were assayed for anti-$G_{17}$ antibodies by radioimmunoassay (RIA). 1.0 ul of sera was added to 300 ul of buffer (1% BSA in phosphate buffered saline with 0.005M EDTA, pH=7.2). To each of these samples was added 100 ul or 3000 CPM of $^{125}$I-labeled $G_{17}$ (NEN, Specific activity=12 uCi/ug). The samples were incubated 1.0 hour at room temperature. We next added 100 ul of Calf Serum (Hyclone Labs), immediately followed by 500 ul of 25% polyethylene glycol-8000 (Sigma). The samples were mixed and then centrifuged for 30 minutes at 500×g at room temperature. The supernatant was discarded, and the pellet suspended in 250 ul of saline at 90° C. The suspension was transferred to 3.0 ml of Scintiverse II [Fisher Scientific] in mini vials for liquid scintillation counting. The samples were counted in a Beckman Liquid Scintillation counter (#LS 5000 LE) for $^{125}$I. The binding capacities of the antisera were calculated from the resulting $^{125}$I counts per sample and are depicted in FIG. 8.

Both of the polymers induced anti-$G_{17}$ antibody responses. Polymer #1, the 2:1 ratio polymer (FIG. 8), induced a very strong response of 56 pg of antigen bound per ul of sera. Polymer #2, the 20:1 ratio polymer (FIG. 8), induced a response that was 10-fold lower. The response induced by polymer #1 is equivalent to that induced by three injections of the $G_{17}$(6)-DT immunogen of Example 2 in rats.

Thus, polymerized synthetic peptides can be used to induce potent anti-$G_{17}$ antibody responses.

EXAMPLE 6

The following example demonstrates that anti-$G_{17}$ antibodies neutralize the tumor stimulatory activity of $G_{17}$ in vitro.

HCT-116 cells (a human colon cancer cell line) were cultured in McCoy's 5a medium (McCoy et al., *Proc. Soc. Exper. Biol. Med.* 100:115–118) supplemented with epidermal growth factor (10 ng/ml), insulin (20 ug/ml), transferrin (4 ug/ul), sodium selenite ($10^{-8}$M), hydrocortisone (2 ug/ml), and triiodothyronine ($4 \times 10^{-10}$M). Subcultures were made once weekly for four weeks by treating cultures with 0.5% Trypsin+0.2% EDTA in Hanks Balanced Salts Solution to remove adherent cells, followed by inoculation of T-75 tissue culture flasks with approximately $1 \times 10^6$ cells. Cultures were maintained under standard conditions (37°, 100% humidity, 5% $CO_2$).

Prior to testing, the HCT-116 cells were synchronized to late $G_0$ phase with thymidine, as follows: the HCT-116 cells were seeded into 24 well culture plates at approximately $1 \times 10^4$ cells per well and incubated overnight in 1 ml supplemented McCoy's medium 5a. The medium was then removed and replaced with fresh supplemented medium. Thymidine was added to 0.8 mM final concentration to each well and the cultures were incubated for 24 hours. At the end of the synchronization period, the medium containing thymidine was replaced with test media as described below.

Figure 10:
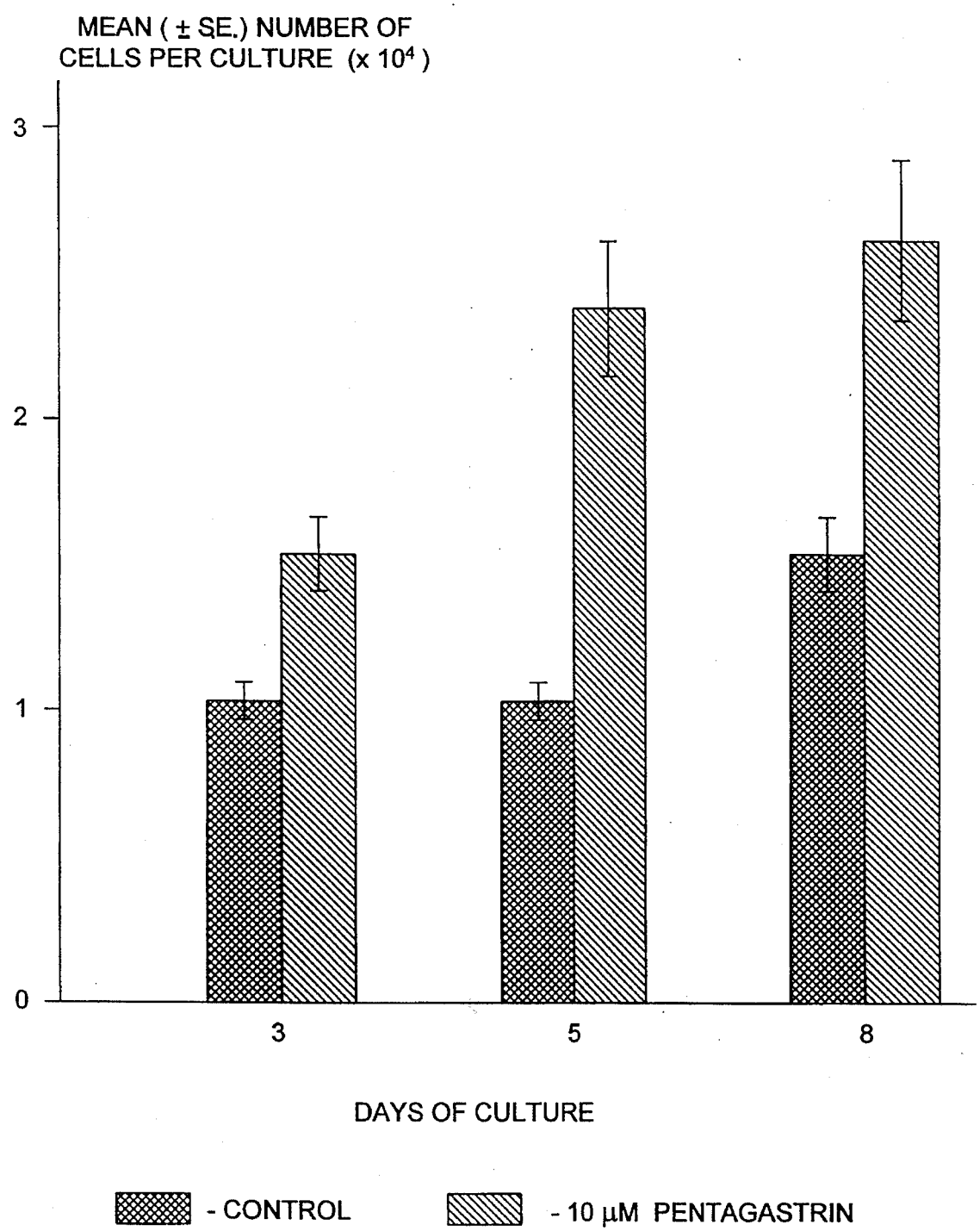
FIG. 10: depicts the stimulation of the growth of human colon cancer cell line, HCT 116, by pentagastrin.

To demonstrate that HCT-116 cells proliferate under the influence of gastrin, the synchronized HCT-116 cells were grown in supplemented McCoy's 5a medium, in the presence or absence of 10 uM pentagastrin (the hormonally active segment of gastrin). To assess cell proliferation, total cell counts were performed after selected incubation times. As shown in FIG. 10, HCT-116 cells proliferated more rapidly in the presence of pentagastrin than in the absence of the hormone. This difference was already evident after three days of culture, and was maximal by day five. The increase in the number of cells of pentagastrin treated culture at the end of eight days was three times greater than that of the non-pentagastrin treated cultures.

To demonstrate that anti-$G_{17}$ antibodies neutralize the proliferative activity of $G_{17}$, the effect of anti-$G_{17}$ antisera upon $G_{17}$-induced increases in the rate of [$^3$H]-thymidine uptake by HCT-116 cells was studied.

Synchronized HCT-116 were cultured in 24 well plates of $10^4$ cells/well in supplemented McCoy's 5a medium without FBS. The total culture volume was 1 ml per well. Four wells were cultured for each test condition. Cells were grown in presence of $G_{17}$ at two concentrations, 5 uM and 50 uM. At each $G_{17}$ concentration, rat anti-human $G_{17}$ antisera (antigen binding capacity determined by RIA=30 pg/ul) or normal rat sera were added at a final dilution of 1:25.

After 8 days of culture, 0.4 uCi of [$^3$H] thymidine (specific activity=2 Ci/mMole) were added to each test well. Following 16 hours incubation, the replicates were processed with a Multiple Automated Cell Harvester (Mini-Mash II, Whittaker Bioproducts) and the [$^3$H]-thymidine incorporation was determined by scintillation counting.

As shown in Table 3, the addition of anti-$G_{17}$ antiserum caused a substantial reduction in [$^3$H]-thymidine incorporation, relative to uptake by cells cultured in the presence of normal rat serum. At 5 uM $G_{17}$, counts incorporated were reduced by 59%; at 50 uM $G_{17}$, label uptake was reduced by 34%. As [$^3$H]-thymidine incorporation directly reflects cell proliferation, this test shows that anti-$G_{17}$ antiserum inhibits the proliferation activity of human $G_{17}$ on colon cancer cells.

TABLE 3

| Quantity of Human $G_{17}$ in Culture | Mean CPM [$^3$H] Thymidine Incorporated (+/− SE) | |
|---|---|---|
| | Normal Rat Serum | Anti-h$G_{17}$ Serum |
| 50 uM | 2130 ± 141 | 1404 ± 310 |
| 5 uM | 1621 ± 131 | 664 ± 206 |

EXAMPLE 7

The following experiment was performed to demonstrate that the growth of established HCT-116 tumors is retarded when nude mice bearing the tumors are treated with anti-gastrin immunoglobin.

Anti-human $G_{17}$ serum was obtained from rats immunized against h$G_{17}$(6)-DT (i.e., Immunogen 1). Normal serum was obtained from nonimmuized rats. Immunoglobulin fractions of the anti-$G_{17}$ serum and the normal rat serum were prepared by affinity chromatography, using Protein A Sepharose. Both immunoglobulin preparations were adjusted to a final protein concentration of 1 mg/ml in PBS. Measured by RIA, the $G_{17}$-direct antigen binding capacity (ABC) of the anti-human $G_{17}$ immunoglobulin preparation was 30 pg/ul. The normal rat immunoglobulin preparation had no anti-human $G_{17}$ activity.

Thirty nude mice were each implanted subcutaneously (dorsally near the left shoulder) by trocar needle (14 gauge) with a single 2 mm cube of HCT-116 tumor tissue. The tumors were allowed to grow for one week prior to random assignment of individual mice to one of three treatment groups, ten mice per group, on day 0 of the Test.

Group I was treated with anti-human $G_{17}$ immunoglobulin function. Each mouse in Group I received intraperitoneal injections of 0.5 mg. of immunoglobulin beginning on day 0 and repeated on days 4, 8, and 14 of the test. The Mean human $G_{17}$ ABC of the mouse sera on day 16 was 8.3±1.3 pg/ul.

Group II was treated with normal rat immuglobulin fraction. Each mouse received intraperitonael injections of 0.5 mg of immunoglobulin beginning on day 0 and repeated on days 4, 9, and 14, of the test. On day 16, the human gastrum $G_{17}$ ABC's of those sera was opg/ul.

Group III received no immunoglobulin injection but was injected instead with saline on days 0, 4, 9, and 14 of the test. The human gastrin $G_{17}$ ABC's of those sera was 0pg./ul. on day 16.

On day 1, mice of Groups I and II were implanted subcutaneously with osmotic pumps (Alzet 2002) that were charged with human $G_{17}$ that delivered 10 ug/day human $G_{17}$ continuously for 14 days. On day 1, mice of Group III were implanted subcutaneously with osmotic pumps charged with saline which delivered a dose of saline instead of hormone continuously for 14 days.

Each mouse was observed daily for changes in the size of their individual tumors. Measurements of the tumors were made by vernier caliper approximately every other day. Volumes of tumors were estimated by the calculation: volume=(length×width$^2$)÷2 (Euhus et. al., 1986, *J. Surg. Oncol.* 31:229–234).

Observations on Group II mice were made through day 17 of the test, on which day the Group II mice were euthanized. Observations on Groups I and II were continued until day 32 of the test.

Figure 11:
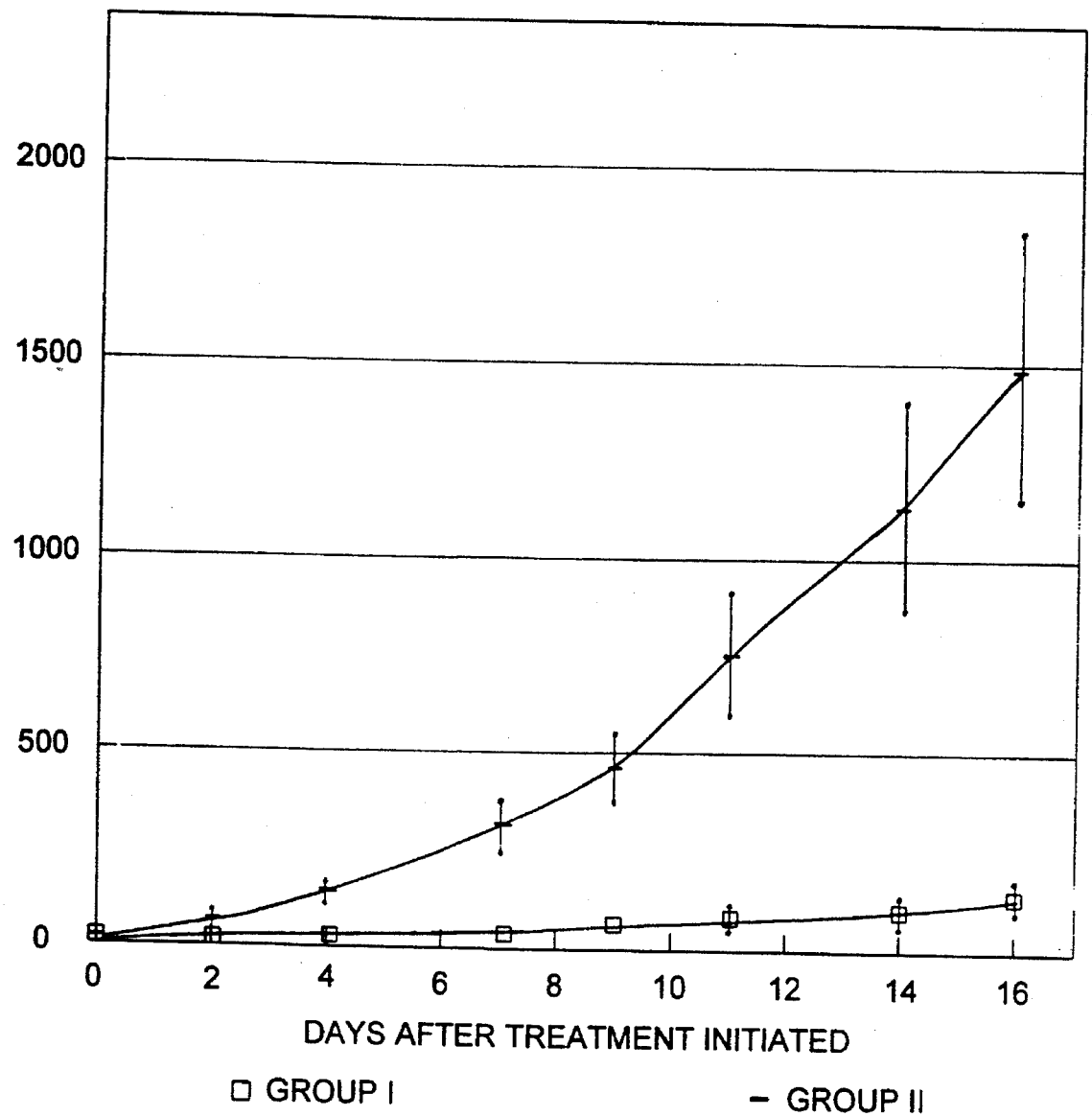
FIG. 11: illustrates the effect of anti-$G_{17}$ antibodies on the growth of colon cancer implants in nude mice infused with $G_{17}$, as measured by mean tumor volume in cubic millimeters. Group I consisted of rats injected with rat anti-$G_{17}$ antibodies, and Group II consisted of rats injected with normal rat antibodies.

As shown in FIG. 11, tumors in Group II mice (administered human $G_{17}$ and treated with normal rat immunoglobulin) grew very rapidly in response to the added gastrin, increasing more than 120 fold in volume in 16 days.

Tumors of Group I mice (administrated human $G_{17}$ and treated with anti-human $G_{17}$ immunoglobulin) grew at a significantly slower rate than the tumors of Group II. By day 16, the volume of the tumors of Group I mice were, on average, approximately 11 times smaller than those of Group II mice (Table 4). The results of this test demonstrate that HCT-116 tumors are stimulated to grow by human gastrin $G_{17}$ and that treatment with anti-human $G_{17}$ specific immunoglobulin neutralizes this growth-promoting effect and significantly slows the growth of HCT-116 tumors.

Figure 12:
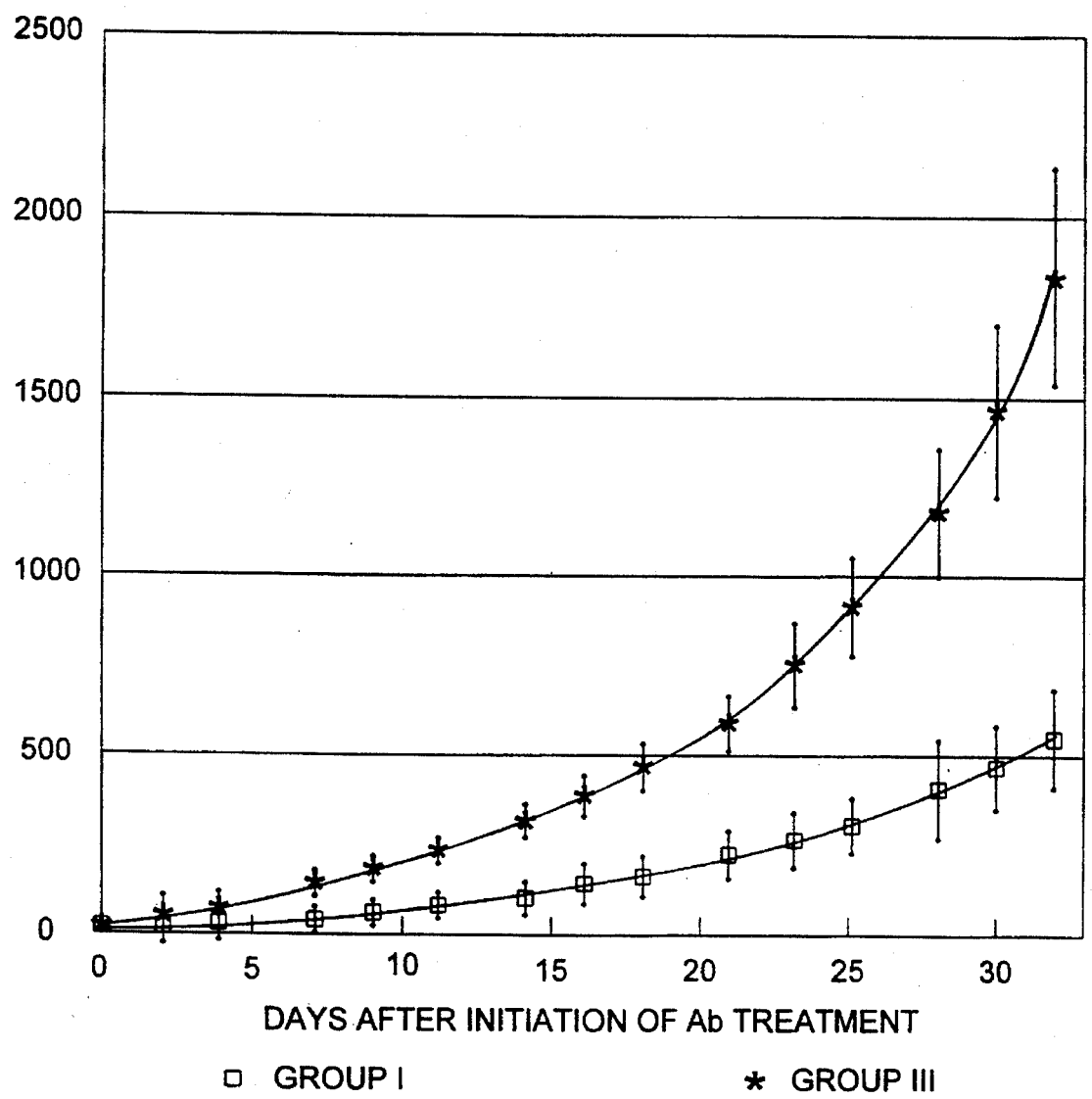
FIG. 12: illustrates the effect of anti-$G_{17}$ on the growth of colon cancer implants in nude mice as measured by mean tumor volumes in cubic millimeters. Group 1 was injected with both $G_{17}$ and anti-$G_{17}$ antibodies. Group III was injected only with saline.

Tumors of Group III mice (not administered h$G_{17}$ and no immunoglobulin treatment) grew at a faster rate than Group I (FIG. 12), suggesting an autocrine production of human $G_{17}$ (by the HCT-116 tumor cells) that stimulated the tumors to grow. Tumor-produced $G_{17}$ would be neutralized in the Group I animals, due to the injected anti-$G_{17}$ immunoglobulins. On day 32 of the test, the Group III tumors had attained approximately the same volume attained by Group II tumors on day 16. However, on day 32 tumors of Group I were significantly smaller than tumors of Group III (i.e., 3.3 times smaller volume, Table 4), indicating an inhibitory effect of the anti-$G_{17}$ immunoglobin on tumor growth.

TABLE 4

| | | Mean Tumor Volume (mm3 ± SE) | |
|---|---|---|---|
| Group | Treatment | day 16 | day 32 |
| I | Anti-$G_{17}$ Antibody plus $G_{17}$ | 142 ± 38 | 545 ± 137 |
| II | Normal Rat Serum plus $G_{17}$ | 1512 ± 348 | — |
| III | Saline and no $G_{17}$ | 391 ± 63 | 1825 ± 313 |

EXAMPLE 8

The following test demonstrates that antibodies against human $G_{17}$ inhibit tumor development and growth in nude mice that have been injected with suspended cells of the human colon cancer line, HCT-116.

Anti-human $G_{17}$ serum was obtained from rats immunized against h$G_{17}$(6)-DT. Normal rat serum was obtained from nonimmunized rats. Immunoglobulin fractions of the anti-$G_{17}$ serum and the normal rat serum were prepared by affinity chromatography, using Protein A Sepharose. Both immunoglobulin preparations were adjusted to a final protein concentration of 1 mg/ml in PBS. Measured by RIA, the $G_{17}$-direct antigen binding capacity (ABC) of the anti-human $G_{17}$ immunoglobulin preparation was 30 pg/ul. The normal rat immunglobulin preparation had no anti-human $G_{17}$ activity.

HCT-116 cells were grown in vitro in the presence of pentagastrin as described in Example 6. Cells in the log phase of growth were collected from in vitro culture, washed by centrifugation in PBS, and resuspended to 10 cells/ml. Viability was assessed by trypan blue exclusion.

Each of 20 nude mice (NIH strain) were injected subcutaneously on their dorsal side near the right shoulder with a single bolus of $5 \times 10^6$ cells.

Two days after the injection of HCT-116 cells, the mice were randomly assigned to two groups of ten mice each. One group (Treated Group) was injected intraperitoneally with 0.5 mg per mouse of the anti-human $G_{17}$ immunoglobulin preparation. The other group (Control Group) was treated with 0.5 mg per mouse of the normal immunoglobulin fraction. Seven days later these treatments were repeated. These treatments resulted in sera $G_{17}$ binding capacities of 11.1 pg/ul in the anti-$G_{17}$ immunoglobulin treated mice and 0 in the normal immunoglobulin treated mice (see Table 5).

Two days after injections of the HCT-116 cells, all of the mice were started on daily injections of human $G_{17}$ for 16 consecutive days. A total daily dose of 51 ug of hormone per mouse was administered in 3 separate injections of 17 ug each, given at 4 hour intervals. The mice were bled on day 16 of the test to determine binding capacities by RIA.

Daily observations on the occurrence and growth of tumors were made visually and by palpation. On day 18 of the test, the tumors were measured by vernier caliper and the volume of each tumor estimated by the following formula: volume=(length×width$^2$)÷2 (Euhus et. al., 1986, *J. Surg. Oncol.* 31:229–234). On Day 18, the mice were euthanized and those mice without visually detectable tumors were dissected and further examined for tumors under a stereo microscope at 10× magnification.

As shown in Table 5, the anti-human $G_{17}$ immunoglobulin prevented tumors from developing in six out of ten mice in the Treated Group. Only one normal immunoglobulin-treated mouse failed to develop a tumor over the course of the test. In the four anti-$G_{17}$ treated animals that developed tumors, the mean tumor volume was reduced greater than four-fold compared to the tumors that developed in the mice treated with normal rat immunglobulin. The Results demonstrate that treatment with anti-human $G_{17}$ immunoglobulin inhibits the development and growth of HCT-116 tumors in nude mice.

TABLE 5

| | Treatment | |
|---|---|---|
| | Normal Rat Immunoglobulin | Anti-$G_{17}$ Immunoglobulin |
| Mean Sera Anti-$G_{17}$ ABC Titer (Range) | 0.0 pg/ul | 11.1 pg/ul (7.6–14.8) |
| Number of Mice Developing Tumors | 9 | 4 |
| Mean Tumor Volume ± S.E. | 21.2 ± 11.2 mm | 4.7 ± 2.8 mm |

EXAMPLE 9

This test demonstrates that antibody-mediated immunity to $G_{17}$ can be selectively and safely reversed by the injection of peptide capable of binding to the antibody.

Six rats that were twice previously immunized with human gastrin $G_{17(6)}$-DT immunogen and which exhibited anti-human gastrin antigen binding capacity of 17–34 pg/ul of serum were prepared for the standard stomach perfusion procedure. To demonstrate that each immunized rat was able to inhibit the acid secretion stimulatory activity of human $G_{17}$, a standard dose of approximately 120 ng of $G_{17}$ hormone was administered to each rat. After measuring the human gastrin $G_{17}$ stimulated acid output in response to the 120 ng of $G_{17}$, a second dose of human gastrin $G_{17}$, of 2.5 ug of hormone at twenty times the first dose was given to each rat and the gastrin stimulated acid output was measured again.

Two of the rats were then euthanized and their kidneys removed for sectioning and examination for deposition of complexes of gastrin and anti-gastrin antibody. Two of the remaining rats were then euthanized and their kidneys removed for sectioning. The remaining two rats were given 250 ug of human gastrin $G_{17}$, were followed for gastrin stimulated acid secretion, and then were euthanized and their kidneys were removed for sectioning.

Figure 9:
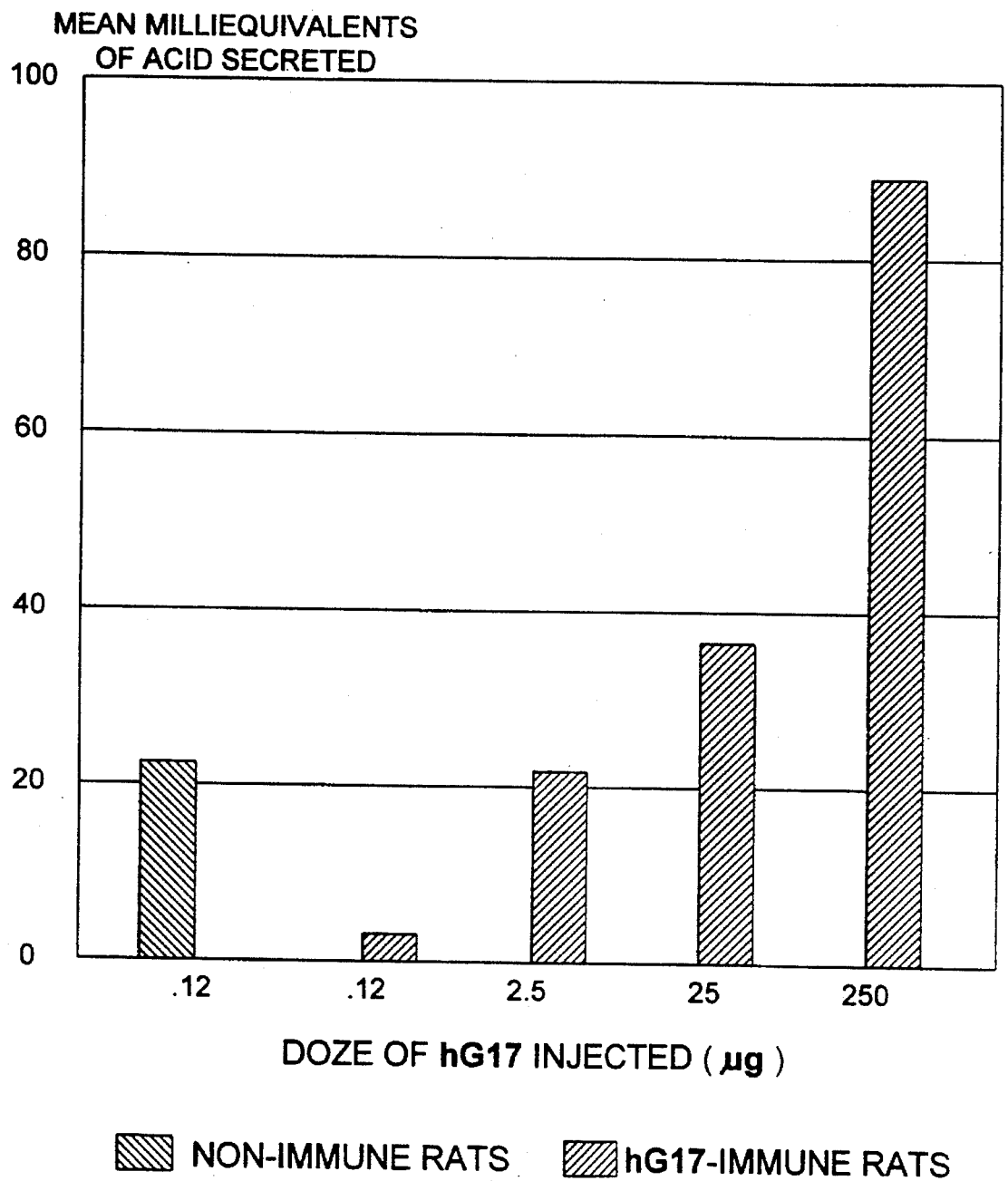
FIG. 9: illustrates the total quantity of stomach acid secreted by $hG_{17}$-immune rats and non-immune rats in response to graded doses of $hG_{17}$. Two non-immune rats and four $hG_{17}$-immune rats were injected with 0.12 micrograms ("ug") and 2.5 ug doses of hG17. Two $hG_{17}$-immune rats were injected with doses of 25 ug and 250 ug of $hG_{17}$.

Rapid reversal of human gastrin $G_{17}$ neutralizing activity of the anti-sera of human gastrin $G_{17}$ immunized rats is demonstrated in FIG. 9. As expected from our previous perfusion assays, administration of approximately 120 ng of human gastrin $G_{17}$ resulted in an 87% mean inhibition of the expected gastrin stimulated acid secretion of all the rats. Challenge with 2.5 ug of human gastrin $G_{17}$ resulted in a gastrin stimulated acid response identical to that seen in non-immunized rats. Challenge with 25 ug or 250 ug of human gastrin $G_{17}$ resulted in an exaggerated acid secretion response. Kidney sections taken from these rats treated with large amounts of human gastrin $G_{17}$ were all negative for formation and deposition of immune complexes.

Treatment of rats immunized with human gastrin $G_{17}$ with only 2.5 ug of human gastrin $G_{17}$ immediately reversed the neutralization of gastrin stimulated acid secretion that was observed in these rats when they were first challenged with 120 ng of human gastrin $G_{17}$. Based on the antigen binding capacities of these rats, which exhibited a range of 17–34 pg/ul and a mean of 24 pg/ul, 2.5 ug of $G_{17}$ is at least a four-fold excess of hormone injected over the total antigen binding capacity of the rat's serum. Such a small amount of hormone, if given in the same proportion based on body weight to humans would amount to a range of only 500–700 ug of human $G_{17}$.

Preferably the antibody neutralizing by infusion would utilize a monovalent neutralizing molecule that bears the gastrin epitope but which does not itself induce acid secretion (e.g., by changing the C-terminal end of $G_{17}$).

The antibody neutralizer will not prevent a renewed production of anti-gastrin antibodies, the duration of which is determined by the conditions of immunization. However, it will neutralize the antibodies as they are produced. In practice, it may be necessary in most cases to provide for neutralization of antibodies synthesized after the initial dose of neutralizing compound is administered. This could be accomplished by means of additional infusions or, preferably, through the administration of the neutralizer in a sustained release compound or device. Although such administration would continue until the synthesis of anti-gastrin antibodies ceases, the quantity of antibody to be neutralized would be significantly less than that eliminated by the first administration of neutralizer. Consequently, the dose/frequency of neutralizer adminstrations would be diminished as antibody production subsides.

This invention and its preferred embodiments have been described in detail. It will be appreciated that those skilled in the art, upon consideration of this disclosure, may make modifications and improvements within the scope of this invention.

We claim:

1. An immunogen which induces a sufficient level of antibodies in an immunized animal to neutralize the physiological effect of the peptide hormone $G_{17}$ in the immunized animal, comprising an immunogenic carrier conjugated by a spacer peptide sequence to the carboxy terminus of a peptide containing a single antigenic epitope cross-reactive with an epitope on the amino terminus of $G_{17}$, which immunogen induces antibodies in the immunized animal which react with an epitope on $G_{17}$ which is present on the first six amino acid residues beginning from the amino terminus of $G_{17}$ and do not cross-react with any other epitope on $G_{17}$ or the peptide hormone $G_{34}$ and prevent the binding of the $G_{17}$ to its physiological receptors in the immunized animal.

2. An immunogen according to claim 1 wherein the carboxy terminus of the peptide is coupled to the immunogenic carrier by a spacer peptide sequence.

3. An immunogen according to claim 1 wherein the peptide is selected from the group consisting of pGlu-Gly-Pro-Trp-Leu-Glu-Glu-Glu-Glu-Glu, and pGlu-Gly-Pro-Trp-Leu-Glu-Glu-Glu-Glu.

4. An immunogen according to claim 2, or 3, wherein the immunogenic carrier is selected from the group consisting of diphtheria toxoid, tetanus toxoid, keyhole limpet hemocyanin, and bovine serum albumin.

5. The immunogen of claims 1, 2, or 3, wherein the immunized animal is a mammal.

6. The immunogen of claim 5, wherein the immunized animal is a human.

7. The immunogen comprising the peptide having the sequence pGlu-Gly-Pro-Trp-Leu-Glu-Glu-Glu-Glu, conjugated by its carboxyl terminal to a spacer peptide sequence which spacer sequence is conjugated to an immunogenic carrier.

8. A pharmaceutical composition comprising an immunogen which comprises an immunogenic carrier conjugated by a spacer peptide sequence to the carboxy terminus of a peptide which contains a single epitope which is cross-reactive with the epitope present on the first six amino acids of the N-terminal amino acid sequence of heptadecagastrin ("$G_{17}$") and a pharmaceutically acceptable carrier or adjuvant.

9. A pharmaceutical composition according to claim 8, wherein the peptide comprises a fragment of the N-terminal amino sequence of $G_{17}$, which is not contained in the N-terminal amino acid sequence of $G_{34}$.

10. A pharmaceutical composition according to claim 8, wherein the peptide is selected from the group consisting of pGlu-Gly-Pro-Trp-Leu-Glu-Glu-Glu-Glu-Glu-Ala-Tyr, pGlu-Gly-Pro-Trp-Leu-Glu-Glu-Glu-Glu-Glu-Ala, pGlu-Gly-Pro-Trp-Leu-Glu-Glu-Glu-Glu-Glu, pGlu-Gly-Pro-Trp-Leu-Glu-Glu-Glu-Glu, pGlu-Gly-Pro-Trp-Leu-Glu-Glu-Glu, pGlu-Gly-Pro-Trp-Leu-Glu-Glu, pGlu-Gly-Pro-Trp-Leu-Glu and pGlu-Gly-Pro-Trp-Leu.

11. A pharmaceutical composition according to claim 8, wherein the immunogenic carrier is selected from the group consisting of diphtheria toxoid, Tetanus Toxoid, keyhole limpet hemocyanin, and bovine serum albumin.

12. A peptide selected from the group consisting of, pGlu-Gly-Pro-Trp-Leu-Glu-Glu-Glu, pGlu-Gly-Pro-Trp-Leu-Glu-Glu, pGlu-Gly-Pro-Trp-Leu-Glu, pGlu-Gly-Pro-Trp-Leu, and pGlu-Gly-Pro-Trp.

13. A pharmaceutical composition comprising of the peptide of claim 12 conjugated by a spacer peptide sequence attached to its carboxy terminal end to an immunogenic carrier.

* * * * *